United States Patent
Green et al.

(10) Patent No.: US 12,281,308 B2
(45) Date of Patent: Apr. 22, 2025

(54) INHIBITION OF PROTEIN KINASES TO TREAT FRIEDREICH ATAXIA

(71) Applicant: University of Massachusetts, Boston, MA (US)

(72) Inventors: Michael R. Green, Boylston, MA (US); Minggang Fang, Northborough, MA (US)

(73) Assignee: University of Massachusetts, Westborough, MA (US)

( * ) Notice: Subject to any disclaimer, the term of this patent is extended or adjusted under 35 U.S.C. 154(b) by 1057 days.

(21) Appl. No.: 17/265,466

(22) PCT Filed: Aug. 29, 2019

(86) PCT No.: PCT/US2019/048771
§ 371 (c)(1),
(2) Date: Feb. 2, 2021

(87) PCT Pub. No.: WO2020/047229
PCT Pub. Date: Mar. 5, 2020

(65) Prior Publication Data
US 2021/0292766 A1 Sep. 23, 2021

Related U.S. Application Data

(60) Provisional application No. 62/724,191, filed on Aug. 29, 2018.

(51) Int. Cl.
*A61K 31/4409* (2006.01)
*A61K 31/472* (2006.01)
(Continued)

(52) U.S. Cl.
CPC ...... *C12N 15/1137* (2013.01); *A61K 31/4409* (2013.01); *A61K 31/472* (2013.01);
(Continued)

(58) Field of Classification Search
CPC ............ C12N 15/1137; C12N 2310/14; C12N 2310/531; C12N 2320/30; C12N 2320/12;
(Continued)

(56) References Cited

U.S. PATENT DOCUMENTS 6,369,086 B1  4/2002 Davis et al.
6,369,087 B1  4/2002 Whittle et al.
(Continued)

FOREIGN PATENT DOCUMENTS

EP   0370498   5/1990
EP   0721331   7/1996
(Continued)

OTHER PUBLICATIONS

Martin, S., "PAN-orama: three convergent views of a eukaryotic deadenylase." Nature Structural & Molecular Biology 21.7 (2014): 577-578.*

(Continued)

*Primary Examiner* — John M Mauro
(74) *Attorney, Agent, or Firm* — Fish & Richardson P.C.

(57) ABSTRACT

Methods that include inhibition of ROCK1/2 and other protein kinases to treat Friedreich Ataxia.

16 Claims, 6 Drawing Sheets

Specification includes a Sequence Listing.

(51) Int. Cl.
*A61K 31/505* (2006.01)
*A61K 31/551* (2006.01)
*C12N 15/113* (2010.01)

(52) U.S. Cl.
CPC .......... *A61K 31/505* (2013.01); *A61K 31/551* (2013.01); *C12N 2310/14* (2013.01); *C12N 2310/531* (2013.01); *C12N 2320/30* (2013.01)

(58) Field of Classification Search
CPC .............. C12N 15/111; A61K 31/4409; A61K 31/472; A61K 31/505; A61K 31/551; A61K 31/713; A61P 25/02; A61P 25/28
See application file for complete search history.

(56) References Cited

U.S. PATENT DOCUMENTS

| | | | |
|---|---|---|---|
| 6,372,733 | B1 | 4/2002 | Caldwell et al. |
| 6,372,778 | B1 | 4/2002 | Tung et al. |
| 7,199,147 | B2 | 4/2007 | Imazaki et al. |
| 7,217,722 | B2 | 5/2007 | Takami et al. |
| 7,563,906 | B2 | 7/2009 | Hagibara et al. |
| 8,071,779 | B2 | 12/2011 | Lampe et al. |
| 8,093,266 | B2 | 1/2012 | Dahmann et al. |
| 8,394,826 | B2 | 3/2013 | DeLong et al. |
| 8,450,344 | B2 | 5/2013 | DeLong et al. |
| 8,637,310 | B2 | 1/2014 | McBride et al. |
| 9,174,939 | B2 | 11/2015 | Alen et al. |
| 2003/0220357 | A1 | 11/2003 | Bankston et al. |
| 2005/0182040 | A1 | 8/2005 | Imazaki et al. |
| 2005/0197328 | A1 | 9/2005 | Bailey et al. |
| 2006/0142193 | A1 | 6/2006 | Wei et al. |
| 2006/0241127 | A1 | 10/2006 | Feurer et al. |
| 2008/0161297 | A1 | 7/2008 | Bosanac et al. |
| 2009/0203678 | A1 | 8/2009 | Mazier et al. |
| 2010/0041645 | A1 | 2/2010 | Dahmann et al. |
| 2010/0137324 | A1 | 6/2010 | Nagarathnam et al. |
| 2010/0183604 | A1 | 7/2010 | Ohta et al. |
| 2011/0166104 | A1 | 7/2011 | Zhou et al. |
| 2011/0294789 | A1 | 12/2011 | Nikolich et al. |
| 2012/0178752 | A1 | 7/2012 | Ginn et al. |
| 2012/0202793 | A1 | 8/2012 | Sweetnam et al. |
| 2012/0270868 | A1 | 10/2012 | Kirrane et al. |
| 2013/0131059 | A1 | 5/2013 | Lampe et al. |
| 2013/0131106 | A1 | 5/2013 | Lampe et al. |
| 2014/0179689 | A1 | 6/2014 | Lawrence et al. |
| 2014/0336440 | A1 | 11/2014 | Schonbrunn et al. |
| 2015/0080472 | A1* | 3/2015 | Gottesfeld .......... C07D 213/75 564/155 |
| 2015/0238601 | A1 | 8/2015 | Boxer et al. |
| 2016/0237095 | A1 | 8/2016 | Kim et al. |
| 2017/0049760 | A1 | 2/2017 | Schonbrunn et al. |
| 2018/0110837 | A1 | 4/2018 | Hafezi-Moghadam et al. |
| 2018/0170939 | A1 | 6/2018 | Accetta et al. |
| 2019/0376064 | A1 | 12/2019 | Green et al. |

FOREIGN PATENT DOCUMENTS

| | | |
|---|---|---|
| EP | 1256578 | 11/2002 |
| EP | 1270570 | 1/2003 |
| EP | 1550660 | 7/2005 |
| EP | 2628482 | 8/2013 |
| WO | WO 1997/023222 | 7/1997 |
| WO | WO 1998/006433 | 2/1998 |
| WO | WO 1999/020620 | 4/1999 |
| WO | WO 1999/064011 | 12/1999 |
| WO | WO 2001/056988 | 8/2001 |
| WO | WO 2002/053143 | 7/2002 |
| WO | WO 2002/076976 | 10/2002 |
| WO | WO 2002/076977 | 10/2002 |
| WO | WO 2003/059913 | 7/2003 |
| WO | WO 2003/062225 | 7/2003 |
| WO | WO 2003/062227 | 7/2003 |
| WO | WO 2003/064397 | 8/2003 |
| WO | WO 2003/082808 | 10/2003 |
| WO | WO 2002/100833 | 9/2004 |
| WO | WO 2004/112719 | 12/2004 |
| WO | WO 2005/003101 | 1/2005 |
| WO | WO 2005/074643 | 8/2005 |
| WO | WO 2007042321 | 4/2007 |
| WO | WO 2008/015001 | 2/2008 |
| WO | WO 2008/021210 | 2/2008 |
| WO | WO 2008/049919 | 5/2008 |
| WO | WO 2009/155209 | 12/2009 |
| WO | WO 2010/104851 | 9/2010 |
| WO | WO 2011/023986 | 3/2011 |
| WO | WO 2011/107608 | 9/2011 |
| WO | WO 2012/135697 | 10/2012 |
| WO | WO 2013/030216 | 3/2013 |
| WO | WO 2013/082548 | 6/2013 |
| WO | WO 2016/094374 | 6/2013 |
| WO | WO 2015/019286 | 2/2015 |
| WO | WO 2016/114655 | 7/2016 |

OTHER PUBLICATIONS

Clay, A., "New developments in pharmacotherapy for Friedreich ataxia." Expert Opinion on Pharmacotherapy 20.15 (2019): 1855-1867.*

Libri, V., "Epigenetic and neurological effects and safety of high-dose nicotinamide in patients with Friedreich's ataxia: an exploratory, open-label, dose-escalation study." The Lancet 384.9942 (2014): 504-513.*

Busi et al., "Exploring frataxin function," IUBMB life, Jan. 2012, 64(1):56-63.

EP Office Action in European Appln. No. 19853524.7, mailed on Sep. 29, 2023, 12 pages.

Gottesfeld et al., "Increasing frataxin gene expression with histone deacetylase inhibitors as a therapeutic approach for Friedreich's ataxia," Journal of Neurochemistry, Aug. 2013, 126:147-54.

Pastore et al., "Frataxin: a protein in search for a function," Journal of Neurochemistry, Aug. 2013, 126:43-52.

Molineris et al., "Drug repositioning for orphan genetic diseases through Conserved Anticoexpressed Gene Clusters (CAGCs)," BMC Bioinformatics, Dec. 2013, 14(1), 10 pages.

Anzovino et al., "Fixing frataxin: 'ironing out' the metabolic defect in Friedreich's ataxia," British Journal of Pharmacology, Apr. 2014, 171(8):2174-90.

Arzate-Mejía et al., "Signaling epigenetics: novel insights on cell signaling and epigenetic regulation," IUBMB Life, Oct. 2011, 63(10):881-95.

Asano et al., "Mechanism of action of a novel antivasospasm drug, HA1077," Journal of Pharmacology and Experimental Therapeutics, Jun. 1, 1987, 241(3):1033-40.

Boerma et al., "Comparative gene expression profiling in three primary human cell lines after treatment with a novel inhibitor of Rho kinase or atorvastatin," Blood Coagulation & Fibrinolysis: An International Journal in Haemostasis and Thrombosis, Oct. 2008, 19(7):709-18.

Boland et al., "3-[2-(Aminomethyl)-5-[(pyridin-4-yl) carbamoyl] phenyl] benzoates as soft ROCK inhibitors," Bioorganic & Medicinal Chemistry Letters, Dec. 1, 2013, 23(23):6442-6.

Bürk et al., "Monitoring progression in Friedreich ataxia (FRDA): the use of clinical scales," Journal of Neurochemistry, Aug. 2013, 126:118-24.

Burridge et al., "A universal system for highly efficient cardiac differentiation of human induced pluripotent stem cells that eliminates interline variability," PloS One, Apr. 8, 2011, 6(4):e18293, 16 pages.

Busskamp et al., "Rapid neurogenesis through transcriptional activation in human stem cells," Molecular Systems Biology, Nov. 2014, 10(11):760.

Caldarella et al., "Feasibility of evaluating quality cancer care using registry data and electronic health records: a population-based study," International Journal for Quality in Health Care, Aug. 1, 2012, 24(4):411-8.

(56) References Cited

OTHER PUBLICATIONS

Campuzano et al., "Friedreich's ataxia: autosomal recessive disease caused by an intronic GAA triplet repeat expansion," Science, Mar. 8, 1996, 271(5254):1423-7.

Chandran et al., "Inducible and reversible phenotypes in a novel mouse model of Friedreich's Ataxia," Elife, Dec. 19, 2017, 6:e30054, 41 pages.

Chutake et al., "Epigenetic promoter silencing in Friedreich ataxia is dependent on repeat length," Annals of Neurology, Oct. 2014, 76(4):522-8.

Defert et al., "Rho kinase inhibitors: a patent review (2014-2016)," Expert Opinion on Therapeutic Patents, Apr. 3, 2017, 27(4):507-15.

Delatycki et al., "Friedreich ataxia: an overview," Journal of Medical Genetics, Jan. 1, 2000, 37(1):1-8.

Evans-Galea et al., "Beyond loss of frataxin: the complex molecular pathology of Friedreich ataxia," Discovery Medicine, Jan. 3, 2014, 17(91):25-35.

Evans-Galea et al., "Cell and gene therapy for Friedreich ataxia: progress to date," Human Gene Therapy, Aug. 1, 2014, 25(8):684-93.

Fang et al., "Common BRAF (V600E)-directed pathway mediates widespread epigenetic silencing in colorectal cancer and melanoma," Proceedings of the National Academy of Sciences, Feb. 2, 2016, 113(5):1250-5.

Fang et al., "The BRAF oncoprotein functions through the transcriptional repressor MAFG to mediate the CpG Island Methylator phenotype," Molecular Cell, Setpember 18, 2014, 55(6):904-15.

Feng et al., "Rho kinase (ROCK) inhibitors and their therapeutic potential," Journal of Medicinal Chemistry, Mar. 24, 2016, 59(6):2269-300.

Fu et al., "The effects of the Rho-kinase inhibitor Y-27632 on arachidonic acid-, GTPγS-, and phorbol ester-induced Ca2+- sensitization of smooth muscle," FEBS Letters, Nov. 27, 1998, 440(1-2):183-7.

Fukiage et al., "Involvement of phosphorylation of myosin phosphatase by ROCK in trabecular meshwork and ciliary muscle contraction," Biochemical and Biophysical Research Communications, Oct. 26, 2001, 288(2):296-300.

Garock-Jones, "Ripasudil: first global approval," Drugs, Dec. 2014, 74(18):2211-5.

Gazin et al., "An elaborate pathway required for Ras-mediated epigenetic silencing," Nature, Oct. 2007, 449(7165):1073-7.

González-Cabo et al., "Friedreich ataxia: an update on animal models, frataxin function and therapies," Inherited Neuromuscular Diseases, Sep. 14, 2009, 247-61.

Gottesfeld, "Small molecules affecting transcription in Friedreich ataxia," Pharmacology & Therapeutics, Nov. 1, 2007, 116(2):236-48.

Harding et al., "Pseudo-dominant' inheritance in Friedreich's ataxia," Journal of Medical Genetics, Aug. 1, 1981, 18(4):285-7.

Huang et al., "Rho/Rho-associated protein kinase signaling pathway-mediated downregulation of runt-related transcription factor 2 expression promotes the differentiation of dental pulp stem cells into odontoblasts," Experimental and Therapeutic Medicine, May 1, 2018, 15(5):4457-64.

Ikenoya et al., "Inhibition of rho-kinase-induced myristoylated alanine-rich C kinase substrate (MARCKS) phosphorylation in human neuronal cells by H-1152, a novel and specific Rho-kinase inhibitor," Journal of Neurochemistry, Apr. 2002, 81(1):9-16.

Ishizaki et al., "Pharmacological properties of Y-27632, a specific inhibitor of rho-associated kinases. Molecular pharmacology," May 1, 2000, 57(5):976-83.

Knipe et al., "The Rho kinases: critical mediators of multiple profibrotic processes and rational targets for new therapies for pulmonary fibrosis," Pharmacological Reviews, Jan. 1, 2015, 67(1):103-17.

Koch et al., "ROCK inhibition in models of neurodegeneration and its potential for clinical translation," Pharmacology & Therapeutics, Sep. 1, 2018, 189:1-21.

Koeppen et al., "Friedreich ataxia: neuropathology revised," Journal of Neuropathology & Experimental Neurology, Feb. 1, 2013, 72(2):78-90.

Ku et al., "Friedreich's ataxia induced pluripotent stem cells model intergenerational GAA• TTC triplet repeat instability," Cell Stem Cell, Nov. 5, 2010, 7(5):631-7.

Li et al., "Activation of frataxin protein expression by antisense oligonucleotides targeting the mutant expanded repeat." Nucleic Acid Therapeutics, February 1. 2018. 28(1):23-33.

Li et al., "Excision of expanded GAA repeats alleviates the molecular phenotype of Friedreich's ataxia," Molecular Therapy, Jun. 1, 2015, 23(6):1055, 36 pages.

Liao et al., "Rho kinase (ROCK) inhibitors," Journal of Cardiovascular Pharmacology, Jul. 2007, 50(1):17-24.

Lin et al., "Approaches of targeting Rho GTPases in cancer drug discovery," Expert Opinion on Drug Discovery, Sep. 2, 2015, 10(9):991-1010.

Lin et al., "Discovery and preclinical development of netarsudil, a novel ocular hypotensive agent for the treatment of glaucoma," Journal of Ocular Pharmacology and Therapeutics, Mar. 1, 2018, 34(1-2):40-51.

Maharshi et al., "Nusinersen: the first option beyond supportive care for spinal muscular atrophy," Clinical Drug Investigation, Sep. 2017, 37(9):807-17.

medchemexpress.com, "GSK269962A (Gsk 269962) is a potent ROCK inhibitor with IC50s of 1.6 and 4 nM for recombinant human ROCK1 and ROCK2 respectively. GSK269962A has anti-inflammatory and vasodilatory activities, " retrieved May 19, 2021 from URL <https://www.medchemexpress.com/gsk269962a.html?src=google-product&gclid=CjwKCAjw1uiEBhBzEiwAO9B_He_ZyDlvN6YzOcB2ZEuYGmOkOkO2ImkYo2ABXv0AbcDp-ngc-BpbRRoC2FMQAvD_BwE>, 3 pages.

Nakagawa et al., "ROCK-I and ROCK-II, two isoforms of Rho-associated coiled-coil forming protein serine/threonine kinase in mice," FEBS letters, Aug. 26, 1996, 392(2):189-93.

Ouellet et al., "Deletion of the GAA repeats from the human frataxin gene using the CRISPR-Cas9 system in YG8R-derived cells and mouse models of Friedreich ataxia," Gene Therapy, May 2017, 24(5):265-74.

Palakurtby et al., "Epigenetic silencing of the RASSF1A tumor suppressor gene through HOXB3- mediated induction of DNMT3B expression," Molecular Cell, Oct. 2009, 36(2):219-30.

Pan et al., "Advances in the development of Rho-associated protein kinase (ROCK) inhibitors," Drug Discovery Today, Dec. 1, 2013, 18(23-24):1323-33.

Pandolfo, "Friedreich ataxia," Archives of Neurology, Oct. 13, 2008, 65(10):1296-303.

PCT International Preliminary Report on Patentability in International Appln. No. PCT/US2019/048771, dated Mar. 2, 2021, 7 pages.

PCT International Search Report and Written Opinion in International Appln. No. PCT/US2019/048771, dated Dec. 16, 2019, 10 pages.

Perdomini et al. "Prevention and reversal of severe mitochondrial cardiomyopathy by gene therapy in a mouse model of Friedreich's ataxia," Nature Medicine, May 2014, 20(5):542-7.

Pianese et al., "Real time PCR quantification of frataxin mRNA in the peripheral blood leucocytes of Friedreich ataxia patients and carriers," Journal of Neurology, Neurosurgery & Psychiatry, Jul. 1, 2004, 75(7):1061-3.

Plasterer et al., "Development of frataxin gene expression measures for the evaluation of experimental treatments in Friedreich's ataxia," PLoS One, May 17, 2013, 8(5):e63958, 9 pages.

Rai et al., "Two new pimelic diphenylamide HDAC inhibitors induce sustained frataxin upregulation in cells from Friedreich's ataxia patients and in a mouse model. PloS one," Jan. 21, 2010, 5(1):e8825, 8 pages.

Ruth et al., "RhoC promotes human melanoma invasion in a PI3K/Akt-dependent pathway," Journal of Investigative Dermatology, Apr. 1, 2006, 126(4):862-8.

Sandi et al., "Epigenetic-based therapies for Friedreich ataxia," Frontiers in Genetics, Jun. 3, 2014, 5:165, 13 pages.

(56) References Cited

OTHER PUBLICATIONS

Sandi et al., "Prolonged treatment with pimelic o-aminobenzamide HDAC inhibitors ameliorates the disease phenotype of a Friedreich ataxia mouse model," Neurobiology of Disease, Jun. 1, 2011, 42(3):496-505.
Sasaki et al., "The novel and specific Rho-kinase inhibitor (S)-(+)-2-methyl-1-1[(4-methyl-5-isoquinoline)sulfonyl]-homopiperazine as a probing molecule for Rho-kinase-involved pathway," Pharmacology & Therapeutics, Feb. 1, 2002, 93(2-3):225-32.
Sehon et al., "Potent, selective and orally bioavailable dihydropyrimidine inhibitors of Rho kinase (ROCK1) as potential therapeutic agents for cardiovascular diseases," Journal of Medicinal Chemistry, Nov. 13, 2008, 51(21):6631-4.
Serra et al., "A KRAS-directed transcriptional silencing pathway that mediates the CpG island methylator phenotype, " Elife, Mar. 12, 2014, 3:e02313, 22 pages.
Sharma et al., "Friedreich ataxia in carriers of unstable borderline GAA triplet-repeat alleles," Annals of Neurology: Official Journal of the American Neurological Association and the Child Neurology Society, Dec. 2004, 56(6):898-901.
Shen et al., "Discovery of novel ROCK1 inhibitors via integrated virtual screening strategy and bioassays," Scientific Reports, Nov. 16, 2015, 5(1):1-4.
Sheridan et al., Epigenetic characterization of the FMR1 gene and aberrant neurodevelopment in human induced pluripotent stem cell models of fragile X syndrome, PloS One, Oct. 12, 2011, 6(10):e26203, 13 pages.
Shimizu et al., "Involvement of nuclear factor-κB activation through RhoA/Rho-kinase pathway in LPS-induced IL-8 production in human cervical stromal cells," MHR: Basic Science of Reproductive Medicine, Jan. 16, 2007, 13(3):181-7.
Soragni et al., "Translating HDAC inhibitors in Friedreich's ataxia," Expert Opinion on Orphan Drugs, Sep. 1, 2016, 4(9):961-70.
Strawser et al., "Therapeutic approaches for the treatment of Friedreich's ataxia," Expert Review of Neurotherapeutics, Aug. 1, 2014, 14(8):947-55.
Takahashi et al., "Localization of the gene coding for ROCK II/Rho kinase on human chromosome 2p24." Genomics, Jan. 15, 1999, 55(2):235-7.
Takami et al., "Design and synthesis of Rho kinase inhibitors (I)," Bioorganic & Medicinal Chemistry, May 1, 2004, 12(9):2115-37.

Tamura et al., "Development of specific Rho-kinase inhibitors and their clinical application," Biochimica et Biophysica Acta (BBA)-Proteins and Proteomics, Dec. 30, 2005, 1754(1-2):245-52.
Uehata et al., "Calcium sensitization of smooth muscle mediated by a Rho-associated protein kinase in hypertension," Nature, Oct. 1997, 389(6654):990-4.
Urrutia et al., "The interplay between iron accumulation, mitochondrial dysfunction, and inflammation during the execution step of neurodegenerative disorders," Frontiers in Pharmacology, Mar. 10, 2014. 5:38, 12 pages.
Vicari et al., "Efficacy and safety of fasudil in patients with stable angina: a double-blind, placebo-controlled, phase 2 trial," Journal of the American College of Cardiology, Nov. 15, 2005, 46(10):1803-11.
Vyas PM, et al., "A TAT-Frataxin fusion protein increases lifespan and cardiac function in a conditional Friedreich's ataxia mouse model," Human Molecular Genetics, Mar. 15, 2012, 21(6):1230-47.
Wajapeyee et al., "Oncogenic RAS directs silencing of tumor suppressor genes through ordered recruitment of transcriptional repressors," Genes & Development, Oct. 15, 2013, 27(20):2221-6.
Willis et al., "Lateral-flow immunoassay for the frataxin protein in Friedreich's ataxia patients and carriers," Molecular Genetics and Metabolism, Aug. 1, 2008, 94(4):491-7.
Wilson, "Therapeutic developments in Friedreich ataxia," Journal of Child Neurology, Sep. 2012. 27(9):1212-6.
Xu et al., "Comparison of FDA approved kinase targets to clinical trial ones: insights from their system profiles and drug-target interaction networks," BioMed Research International, Oct. 2016, vol. 2016, 9 pages.
Yarrow et al., "Screening for cell migration inhibitors via automated microscopy reveals a Rho-kinase inhibitor." Chemistry & Biology, Mar. 1, 2005, 12(3):385-95.
EP Extended Search Report in European Appln. No. 19853524.7, dated Apr. 13, 2022, 12 pages.
Yamaguchi et al., Molecular mechanism for the regulation of rho-kinase by dimerization and its inhibition by fasudil. Structure, Mar. 1, 2006, 14(3):589-600.
González-Fernández et al., "Phosphodiesterase inhibitors as Friedreich's ataxia treatment," 18th National Competition for Scientific and Technical Research, Mar. 1, 2016, 2 pages.

* cited by examiner

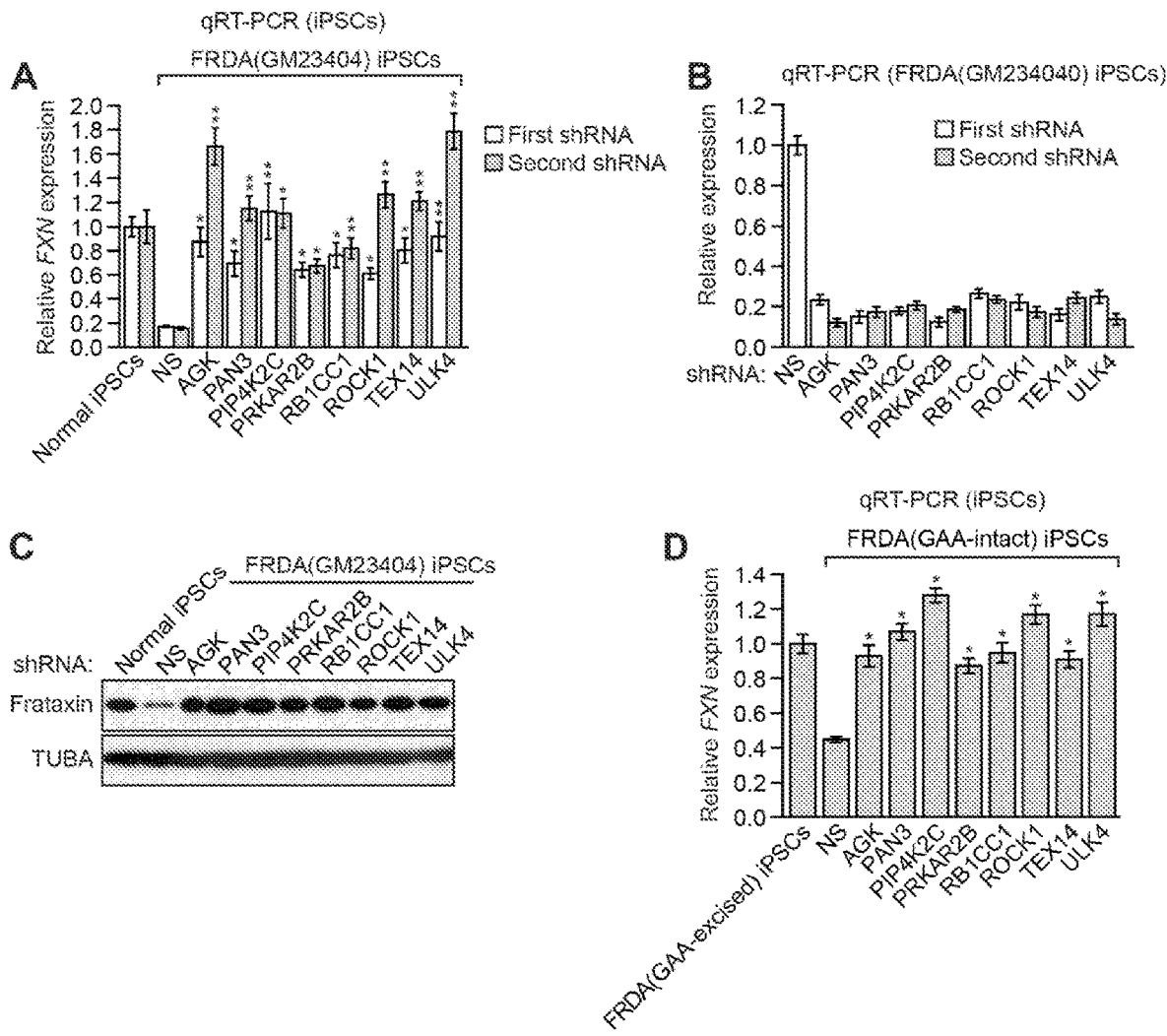
FIGs. 1A-D

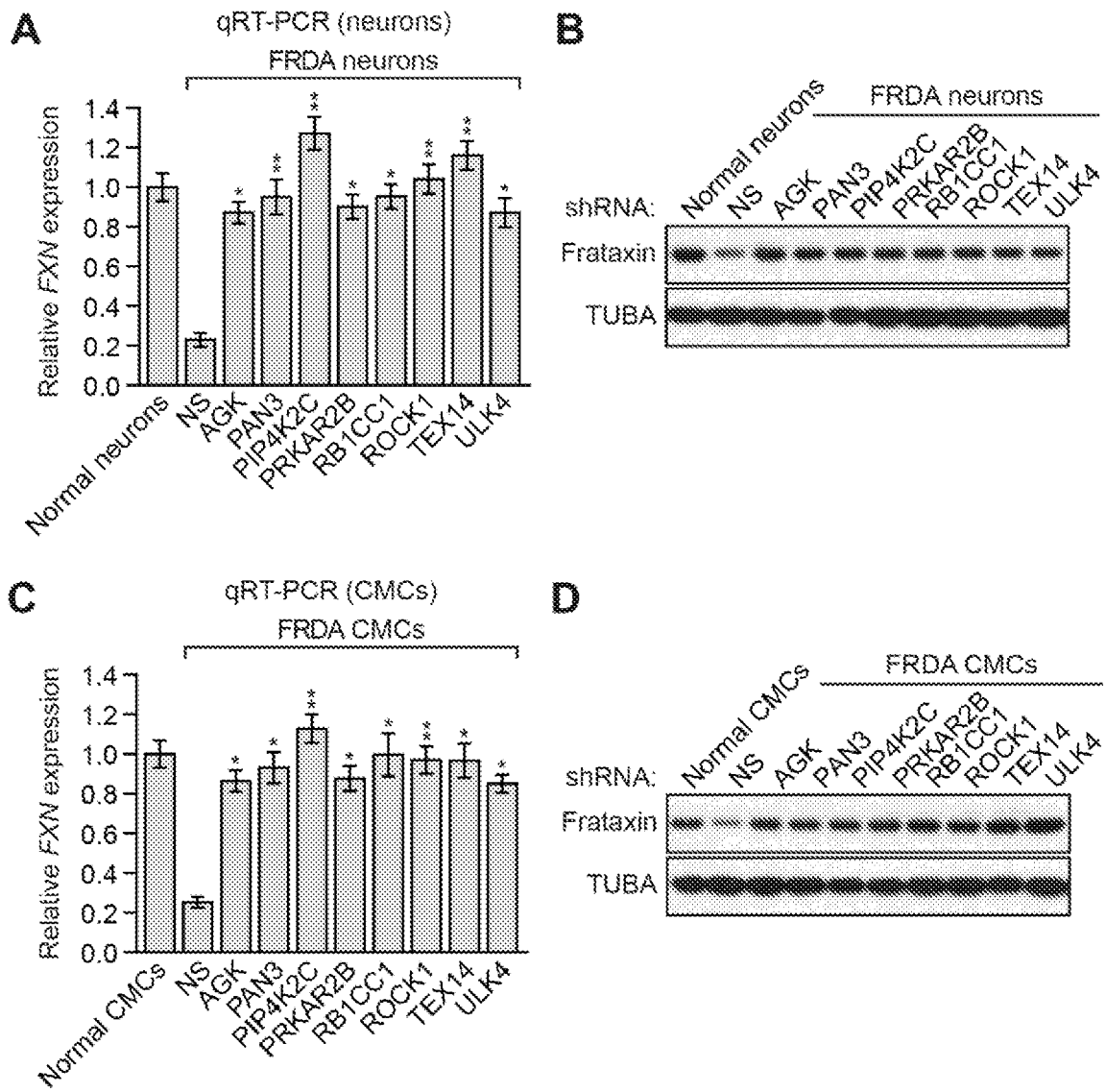
FIGs. 2A-D

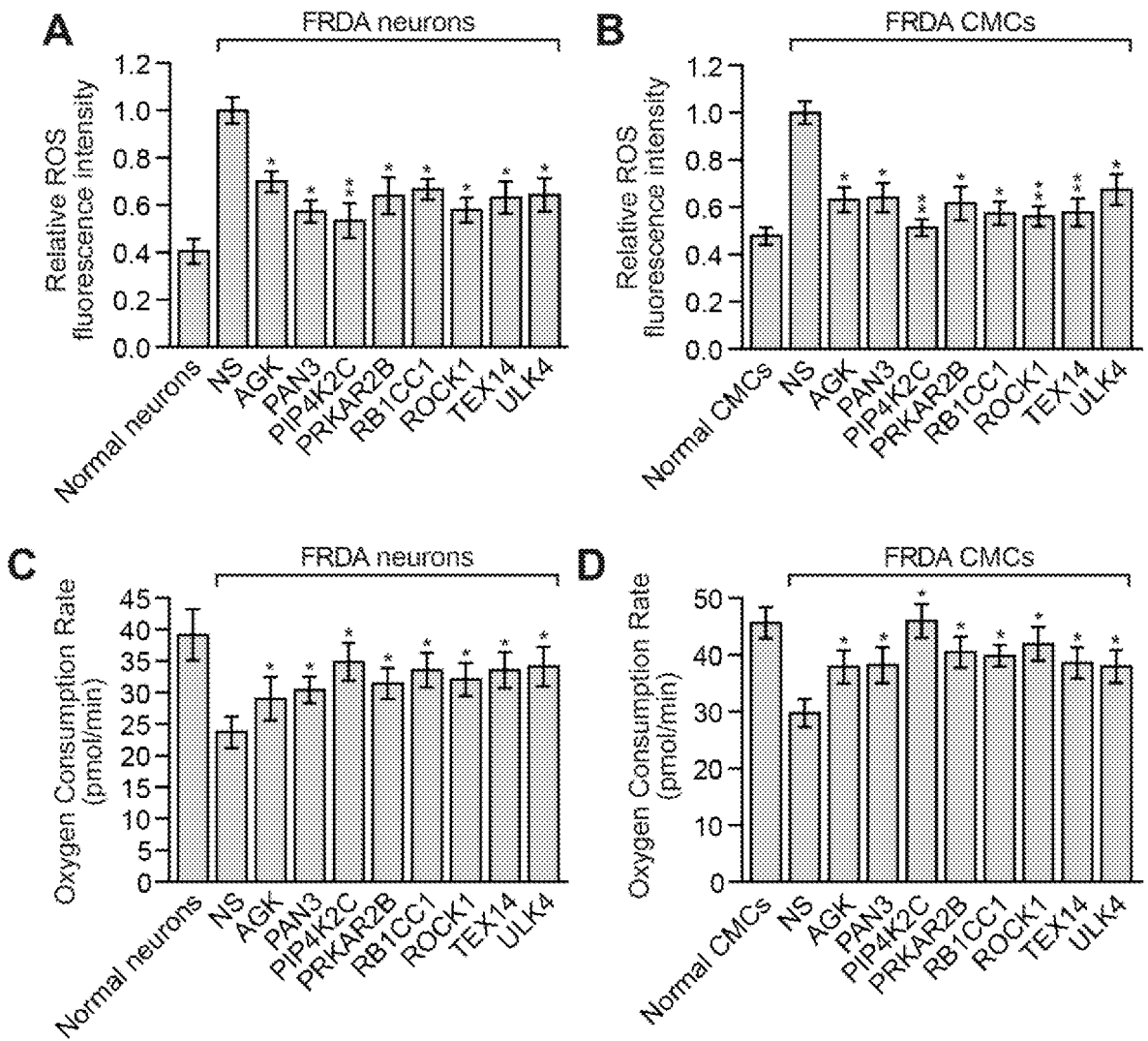
FIGs. 3A-D

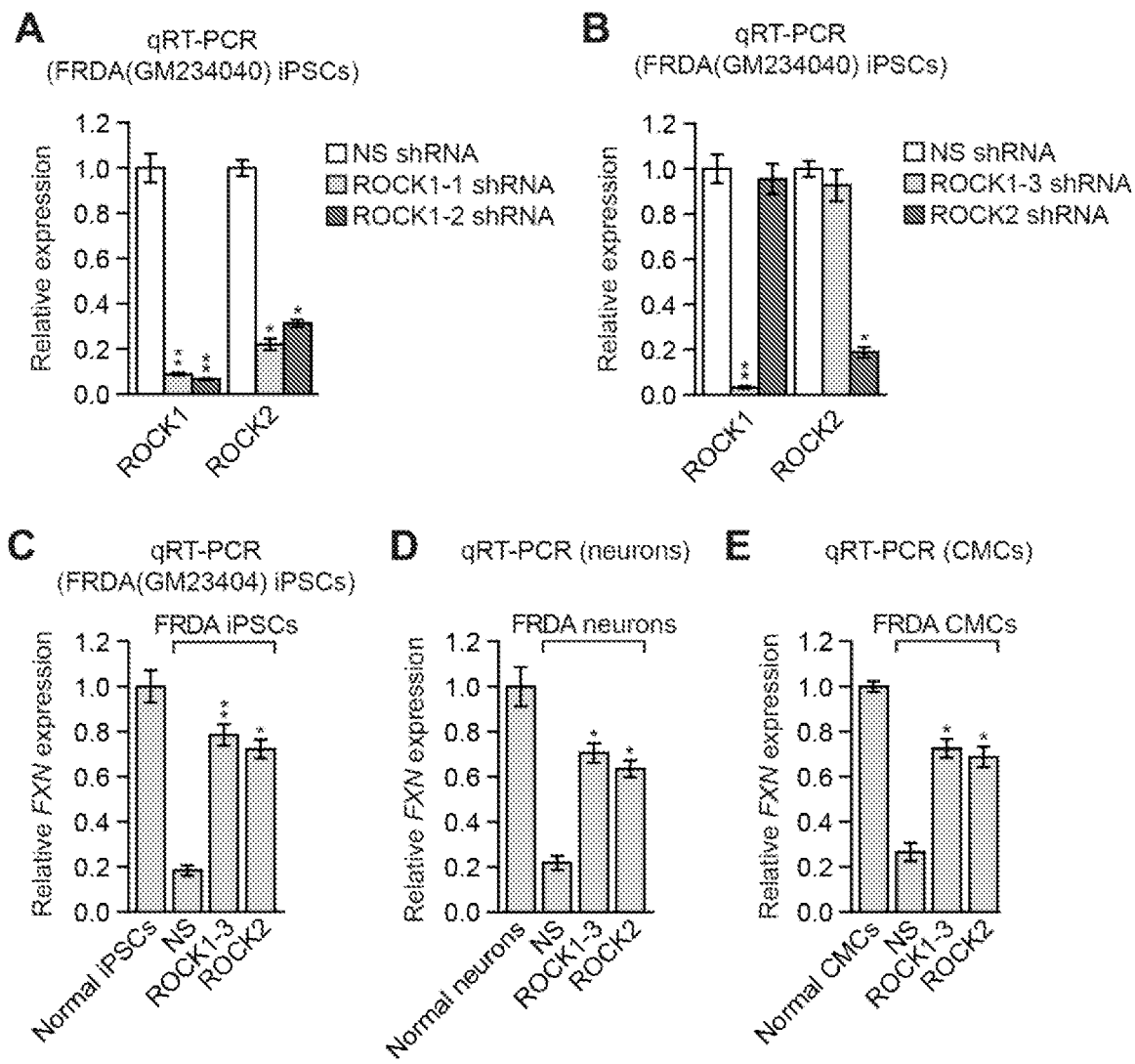
FIGs. 4A-E

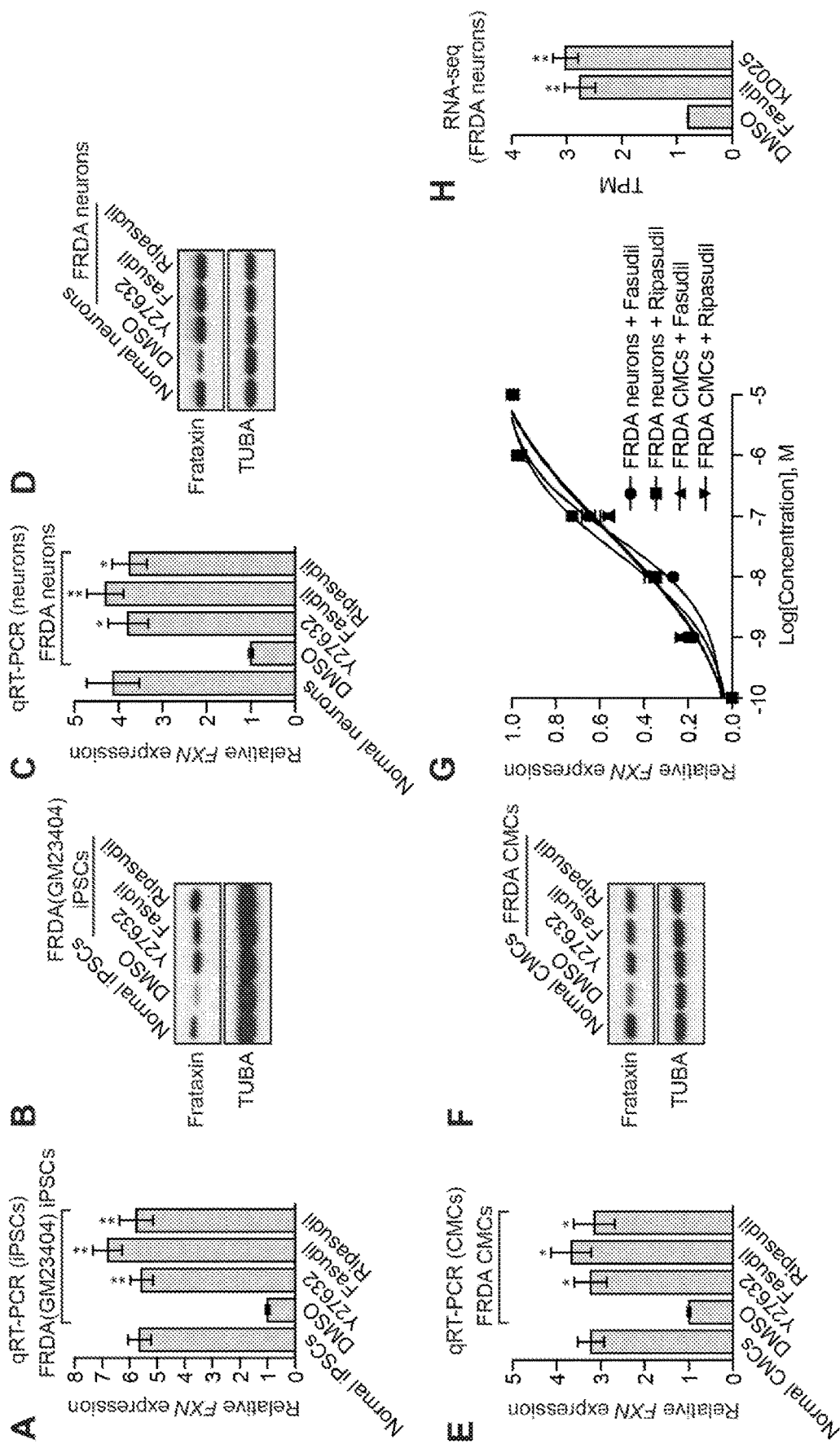
FIGs. 5A-H

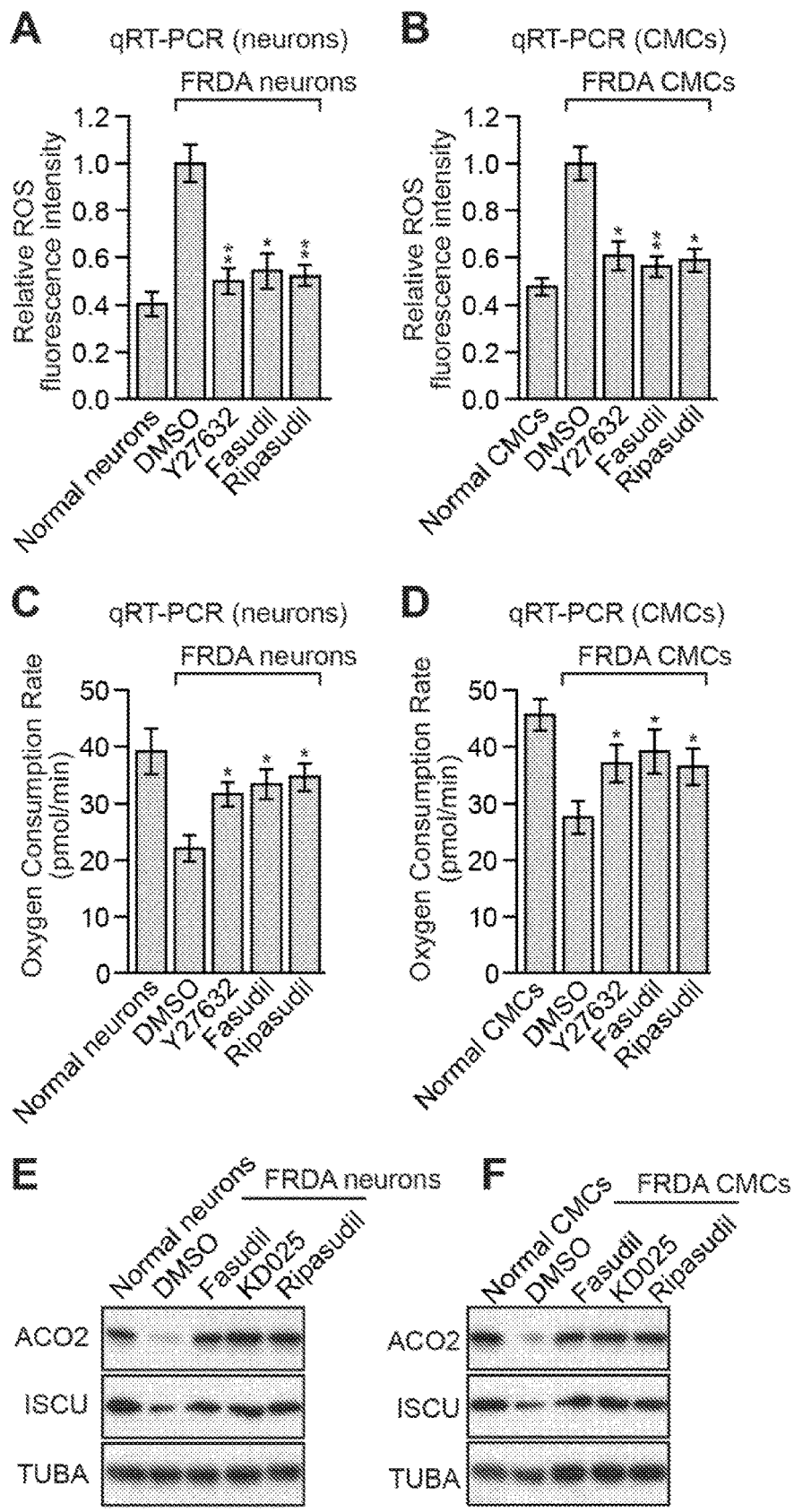
FIGs. 6A-F

INHIBITION OF PROTEIN KINASES TO TREAT FRIEDREICH ATAXIA

CLAIM OF PRIORITY

This application is a National Stage Application under 35 U.S.C. § 371 of International Application No. PCT/US2019/048771, filed Aug. 29, 2019, which claims the benefit of U.S. Provisional Patent Application Ser. No. 62/724,191, filed Aug. 29, 2018. The entire contents of the foregoing are hereby incorporated by reference.

TECHNICAL FIELD

Described herein are methods that include inhibition of ROCK1/2 and other protein kinases to treat Friedreich Ataxia.

SEQUENCE LISTING

The instant application contains a Sequence Listing which has been submitted electronically in ASCII format and is hereby incorporated by reference in its entirety. Said ASCII copy, created on Jan. 27, 2021, is named 0410US1SeqList.txt and is 4272 bytes in size.

BACKGROUND

Friedreich ataxia (also called Friedreich's ataxia) (FRDA) is an autosomal recessive inherited disease characterized by progressive damage to the nervous system and severe cardiac abnormalities (Delatycki et al., J Med Genet, 2000, 37 (1): 1-8). FRDA is the most common genetic form of ataxia, and occurs in approximately 1 in 50,000 people. Symptoms typically first appear at 5-15 years of age, followed by progressive neurodegeneration. Generally, within 10 years following the onset of symptoms, the patient is wheelchair bound. The disease affects multiple organs, including the heart and pancreas. Patients have a shortened life expectancy, with most patients dying of cardiac failure. To date, there is no effective therapy for FRDA, and only palliative treatments are available (Wilson, J Child Neurol, 2012, 27 (9): 1212-1216; Evans-Galea et al., Hum Gene Ther, 2014, 25 (8): 684-693: Strawser et al., Expert Rev Neurother. 2014, 14 (8): 949-957). Therefore, identification of a treatment for FRDA represents a major unmet medical need.

SUMMARY

As shown herein, a number of protein kinases that are targets for discovery of biological or small molecule inhibitors will increase transcription of the mutant FXN gene. In addition, we have shown that small molecule ROCK1/2 inhibitors (e.g., fasudil, ripasudil, and Y27632) increase transcription of the mutant FXN gene and ameliorate mitochondrial dysfunction, which has immediate therapeutic implications. Thus, provided herein are methods for treating a subject having a disorder associated with a mutation in the FXN gene and having reduced expression of frataxin protein. The methods include administering to the subject a therapeutically effective amount of an inhibitor of a FXN Repressing Factor (FXN-RF) selected from the group consisting of acylglycerol kinase (AGK): poly(A) specific ribonuclease subunit (PAN3): phosphatidylinositol-5-phosphate 4-kinase type 2 gamma (PIP4K2C): protein kinase cAMP-dependent type II regulatory subunit beta (PRKAR2B): RB1 inducible coiled-coil 1 (RB1CC1); rho associated coiled-coil containing protein kinase 1 (ROCK1): rho associated coiled-coil containing protein kinase 2 (ROCK2); testis expressed 14, intercellular bridge forming factor (TEX14); and unc-51 like kinase 4 (ULK4).

Also provided herein are inhibitors of a FXN Repressing Factor (FXN-RF) selected from the group consisting of acylglycerol kinase (AGK): poly(A) specific ribonuclease subunit (PAN3): phosphatidylinositol-5-phosphate 4-kinase type 2 gamma (PIP4K2C): protein kinase cAMP-dependent type II regulatory subunit beta (PRKAR2B): RB1 inducible coiled-coil 1 (RBICC1); rho associated coiled-coil containing protein kinase 1 (ROCK1); rho associated coiled-coil containing protein kinase 2 (ROCK2): testis expressed 14, intercellular bridge forming factor (TEX14): and unc-51 like kinase 4 (ULK4), for use in a method of treating a subject having a disorder associated with a mutation in the FXN gene and having reduced expression of frataxin protein.

In some embodiments, the subject has (e.g., has been diagnosed with) Friedreich ataxia (FRDA).

In some embodiments, the inhibitor is an inhibitor of ROCK1/2, e.g., a small molecule inhibitor of ROCK1/2. In some embodiments, the small molecule inhibitor of ROCK1/2 is a cyclohexanecarboxamide (e.g., Y-27632 ((+)-(R)-trans-4-(1-aminoethyl)-N-(4-pyridyl)cyclohexanecarboxamide dihydrochloride) and Y-30131 ((+)-(R)-trans-4-(1-aminoethyl)-N-(1H-pyrrolo[2, 3-b]pyridin-4-yl) cyclohexanecarboxamide dihydrochloride)): a dihydropyrimidinones or dihydropyrimidine (e.g., bicyclic dihydropyrimidine-carboxamides; ureidobenzamide (e.g., CAY10622 (3-[[[[[4-(aminocarbonyl)phenyl]amino]carbonyl]amino]methyl]-N-(1, 2, 3, 4-tetrahydro-7-isoquinolinyl)-benzamide)); Thiazovivin; GSK429286A; RKI-1447 (1-(3-Hydroxy benzyl)-3-(4-(pyridin-4-yl)thiazol-2-yl) urea); GSK180736A (GSK180736); Hydroxyfasudil (HA-1100); OXA 06; Y-39983; Netarsudil (AR-13324); GSK269962/GSK269962A; indazole derivatives including Y27632 and isoquinoline sulfonyl derivatives (e.g., fasudil (HA-1077, 1-(5-isoquinolinesulfonyl)-homopiperazine) or a derivative that shares the core structure of 5-(1,4-diazepan-1-ylsulfonyl) isoquinoline e.g., ripasudil (K-115, 4-fluoro-5-[[(2S)-2-methyl-1,4-diazepan-1-yl]sulfonyl]isoquinoline): KD025 (SLx-2119) or related compound XD-4000; SR 3677; AS 1892802; H-1152 ((S)-(+)-2-Methyl-1-[(4-methyl-5-isoquinolinyl) sulfonyl]homopiperazine); N-(4-Pyridyl)-N'-(2,4,6-trichlorophenyl)urea); 3-(4-Pyridyl)-1H-indole: 3-[2-(aminomethyl)-5-[(pyridin-4-yl)carbamoyl] phenyl]benzoates (e.g., AMA0076); TC-S 7001; AT13148; inhibitors with the scaffold 4-Phenyl-1H-pyrrolo[2,3-b]pyridine, including compound TS-f22; heterocyclic amino derivatives; indazole derivatives disclosed in WO 02/100833; pyridylthiazole urea; quinazoline derivatives; and pharmaceutically acceptable salts thereof. In some embodiments, the small molecule inhibitor of ROCK1/2 is fasudil, ripasudil or Y27632. In some embodiments, the small molecule inhibitor of ROCK2 is KD025.

In some embodiments, the inhibitor is an inhibitory nucleic acid that targets and specifically reduces expression of ROCK1/2, e.g., a small interfering RNA, small hairpin RNA, or antisense oligonucleotide. In some embodiments, the inhibitory nucleic acid is modified.

Unless otherwise defined, all technical and scientific terms used herein have the same meaning as commonly understood by one of ordinary skill in the art to which this invention belongs. Methods and materials are described herein for use in the present invention: other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 1A-D. Identification of protein kinases that mediate repression of the mutant FXN gene in FRDA iPSCs. (A) qRT-PCR analysis monitoring FXN transcription in FRDA (GM23404) iPSCs expressing one of two unrelated shRNAs targeting 8 protein kinases. The results were normalized to that obtained with normal iPSCs, which was set to 1. (B) qRT-PCR analysis monitoring shRNA knockdown efficiencies. (C) Immunoblot analysis showing frataxin levels in FRDA (GM23404) iPSCs expressing an NS or a protein kinase FXN-RF shRNA. Frataxin levels in normal iPSCs are shown. α-tubulin (TUBA) was monitored as a loading control. (D) qRT-PCR analysis monitoring FXN transcription in FRDA (GAA-intact) iPSCs. The results were normalized to that obtained with FA (GAA-excised) iPSCs, which was set to 1. Data are represented as mean+SD (n=3 technical replicates of a representative experiment (out of 3 independent experiments)). *P<0.05, **P<0.01.

FIGS. 2A-D. The protein kinase FXN-RFs also mediate epigenetic repression of the mutant FXN gene in post-mitotic FRDA neurons and cardiomyocytes. (A, B) qRT-PCR analysis monitoring FXN transcription (A) and immunoblot analysis showing frataxin levels (B) in FRDA neurons expressing an shRNA targeting a protein kinase FXN-RF. (C, D) qRT-PCR analysis monitoring FXN transcription (C) and immunoblot analysis showing frataxin levels (D) in FRDA cardiomyocytes (CMCs) expressing an shRNA targeting a protein kinase FXN-RF. Data are represented as mean+SD (n=3 technical replicates of a representative experiment (out of 3 independent experiments)). *P<0.05, **P<0.01.

FIGS. 3A-D. Inhibition of protein kinase FXN-RFs can ameliorate characteristic mitochondrial defects of FRDA post-mitotic neurons and cardiomyocytes. (A, B) Quantification of flow cytometry analysis of normal and FRDA neurons (A) or normal and FRDA CMCs (B) expressing an FXN-RF shRNA and stained with MitoSOX. (C, D) Analysis of the mitochondrial oxygen consumption rate in normal and FRDA neurons (C) or normal and FRDA CMCs (D) expressing an FXN-RF shRNA. Data are represented as mean+SD (n=3 technical replicates of a representative experiment (out of 3 independent experiments)). *P<0.05. **P<0.01.

FIGS. 4A-E. Identification of ROCK2 as a protein kinase that mediates repression of the mutant FXN gene. (A) qRT-PCR analysis monitoring ROCK1 and ROCK2 expression in FRDA (GM23404) iPSCs expressing the two ROCK1 shRNAs used in the experiments shown in FIGS. 1-3 (hereafter called ROCK1-1 and ROCK1-2). The results reveal that the ROCK1-1 and ROCK1-2 shRNAs knocked down both ROCK1 and ROCK2. (B) qRT-PCR analysis monitoring knockdown efficiencies of selective ROCK1 (ROCK1-3) and ROCK2 shRNAs. (C) qRT-PCR analysis monitoring FXN transcription in FRDA (GM23404) iPSCs expressing a selective ROCK1 or ROCK2 shRNA. The results were normalized to that obtained with normal iPSCs, which was set to 1. (D, E) qRT-PCR analysis monitoring FXN transcription in FRDA neurons (D) and FRDA CMCs (E) expressing a selective ROCK1 or ROCK2 shRNA.

FIGS. 5A-H. Transcriptional upregulation of the mutant FXN gene by small molecule ROCK1/2 inhibitors in FRDA iPSCs, neurons and cardiomyocytes. (A-F) qRT-PCR analysis monitoring FXN transcription and immunoblot analysis showing frataxin protein levels in FRDA (GM23404) iPSCs (A, B), FRDA neurons (C, D) or FRDA CMCs (E, F) treated with fasudil (1 μM), ripasudil (0.5 μM), Y27632 (0.5 μM) or, as a control, DMSO. (G) Dose response curves in FRDA neurons and CMCs treated with fasudil or ripasudil. (H) Results of massively parallel short-read sequencing analysis showing FXN transcript levels in FRDA neurons treated with DMSO, fasudil or KD025. TPM, transcripts per million. Data are represented as mean±SD (n=3 technical replicates of a representative experiment (out of 3 independent experiments)). *P<0.05, **<0.01.

FIGS. 6A-F. Transcriptional upregulation of the mutant FXN gene by small molecule ROCK1/2 inhibitors in FRDA neurons and cardiomyocytes. (A, B) Quantification of flow cytometry analysis of FRDA neurons (A) or FRDA CMCs (B) treated with fasudil (1 μM), ripasudil (0.5 μM), Y27632 (0.5 μM) or, as a control, DMSO, and stained with MitoSOX. (C, D) Analysis of the mitochondrial oxygen consumption rate in FRDA neurons (C) or FRDA CMCs (D) treated with a small molecule ROCK1/2 inhibitor. (E, F) Immunoblot analysis showing levels of mitochondrial proteins ACO and ISCU in FRDA neurons (E) or FRDA CMCs (F) treated with fasudil (1 μM), KD025 (1 μM), or ripasudil (0.5 μM). Data are represented as mean±SD (n=3 technical replicates of a representative experiment (out of 3 independent experiments)). *P<0.05, **<0.01.

DETAILED DESCRIPTION

FRDA is caused by a GAA·TTC triplet repeat expansion in the first intron of the FXN gene (hereafter called the mutant FXN gene) (Campuzano et al., Science, 1996, 271 (5254): 1423-1427). Unaffected individuals have 6-30 GAA·TTC repeats, whereas affected individuals have approximately 70-1000 repeats (Sharma et al., Ann Neurol, 2004, 56 (6): 898-901: Pandolfo, Arch Neurol, 2008, 65 (10): 1296-1303). The effect of the GAA·TTC repeat expansion mutation is to reduce expression of frataxin at the level of transcription, through the formation of heterochromatin and subsequent gene repression. The extent of FXN repression is directly related to the length of the GAA·TTC repeat: age of onset and disease severity are also correlated with the length of the GAA·TTC repeat (Chutake et al., Ann Neurol, 2014, 76 (4): 522-528).

The FXN gene encodes a protein called frataxin, a ubiquitous, nuclear-encoded mitochondrial protein that plays a key role in iron-sulfur (Fe—S) cluster biosynthesis and iron homeostasis (Anzovino et al., Br J Pharmacol, 2014, 171 (8): 2174-2190). Importantly, the mutant FXN gene encodes a normal, functional frataxin protein, which is present at reduced levels. The reduction in frataxin levels results in mitochondrial dysfunction, which is thought to be the main driver of disease pathology, with mitochondria-rich tissues such as the heart and nervous system being the most severely affected (Evans-Galea et al., Discov Med, 2014, 17 (91): 25-35). Neurological symptoms are caused by degeneration of sensory neurons in the dorsal root ganglia and in the dentate nucleus of the cerebellum (Koeppen and Mazurkiewicz, J Neuropathol Exp Neurol, 2013, 72 (2): 78-90).

The scientific premise of our work is that inducing a more permissive chromatin state in the epigenetically repressed mutant FXN gene in FRDA patients will result in increased transcription of mutant FXN and decreased disease symptomatology. An important feature of this therapeutic approach is that it is based on correcting the root cause of the disease, the decreased levels of frataxin, rather than some secondary, downstream consequence of the frataxin deficiency, such as mitochondrial dysfunction. Notably, the level of frataxin in FRDA patients is only a few-fold lower than that in asymptomatic carriers, who harbor one mutant FXN allele and one normal FXN allele (Pianese et al., J Neurol Neurosurg Psychiatry. 2004, 75 (7): 1061-1063). Thus, only a modest increase in transcription of the mutant FXN gene is required to restore normal levels of frataxin. In addition, as mentioned above, the severity of the disease is correlated with the extent of frataxin reduction (Chutake et al., Ann Neurol, 2014, 76 (4): 522-528). Thus, any increase in frataxin levels is predicted to have at least some therapeutic benefit. As shown herein, shRNAs and small molecules can increase transcription of the mutant FXN gene 2-6-fold, which is predicted to be within or above the minimal therapeutic level.

Several lines of evidence, both from other groups and our results, strongly support the feasibility of upregulating mutant FXN transcription as a therapeutic approach. First, the notion that inducing a more permissive chromatin state will increase mutant FXN expression is supported by studies showing that HDAC inhibitors can upregulate transcription of the mutant FXN gene (Rai et al., PLOS One. 2010, 5 (1):e8825: Sandi et al., Neurobiol Dis, 2011, 42 (3): 496-505). In addition, CRISPR-mediated deletion of the GAA·TTC repeat expansion of mutant FXN restores FXN transcription and frataxin levels (Ouellet et al., Gene Ther, 2017, 24 (5): 265-274). Most importantly, as we previously demonstrated (U.S. Application No. 62/464,557, Genetic and Pharmacological Transcriptional Upregulation of the Repressed FXN Gene as a Therapeutic Strategy for Friedreich Ataxia), we have identified 10 epigenetic regulators that mediate repression of the mutant FXN gene (which we refer to as FXN Repressing Factors, or FXN-RFs) and shown that short hairpin RNAs (shRNAs) or small molecule inhibitors targeting these FXN-RFs upregulate mutant FXN transcription and increase frataxin levels in induced pluripotent stem cells (iPSCs), neurons and cardiomyocytes derived from FRDA patients.

Second, the idea that upregulating mutant FXN transcription will decrease disease symptomology is supported by studies showing that in frataxin-deficient adult mice restoration of normal frataxin levels, even after the development of severe symptoms, substantially ameliorates disease phenotypes, in both the heart (Perdomini et al., Nat Med. 2014, 20 (5): 542-547; Chandran et al. 2017, eLife 6:e30054) and nervous system (Chandran et al. 2017, eLife 6:e30054), and motor coordination deficits (Chandran et al. 2017, eLife 6:e30054), indicating that characteristic FRDA symptoms are reversible. In addition, HDAC inhibitors that upregulate mutant FXN expression ameliorate disease phenotypes in FRDA mice (Rai et al., PLOS One. 2010, 5 (1):e8825; Sandi et al., Neurobiol Dis, 2011, 42 (3): 496-505). Finally, we have demonstrated that inhibition of FXN-RFs by shRNAs or small molecules can correct mitochondrial defects of FRDA neurons and cardiomyocytes (U.S. Application No. 62/464,557, Genetic and Pharmacological Transcriptional Upregulation of the Repressed FXN Gene as a Therapeutic Strategy for Friedreich Ataxia).

Studies from our lab (Gazin et al., Nature, 2007, 449 (7165): 1073-1077: Palakurthy et al., Mol Cell. 2009, 36 (2): 219-230; Wajapeyee et al. Genes Dev, 2013, 27 (20): 2221-2226; Serra et al., eLife, 2014, 3: e02313: Fang et al., Mol Cell, 2014, 55 (6): 904-915; Fang et al., Proc Natl Acad Sci USA, 2016, 113 (5): 1250-1255) and others (Arzate-Mejia et al., IUBMB Life, 2011, 63 (10:881-895) have shown that in addition to chromatin-bound epigenetic regulators, transcriptional repression can also be promoted by "upstream" non-chromatin associated factors, such as cell signaling proteins. These upstream factors can function by modulating the activity of epigenetic regulators and can include highly druggable targets such as protein kinases. As of 2016, 35 small molecule protein kinase inhibitors have been approved as drugs by the United States Food and Drug Administration (US FDA) (Xu et al., Biomed Res Int, 2016, 2016:2509385). In this invention disclosure, we describe the identification of 8 protein kinases as new FXN-RFs. We expect our findings to have a major impact on the field of FRDA therapeutics and have the potential to lead to development of a new class of drugs to treat this devastating disease.

Alternative approaches for restoring normal levels of frataxin in FRDA patients include gene therapy (Perdomini et al., Nat Med, 2014, 20 (5): 542-547) and protein replacement therapy (Vyas et al., Hum Mol Genet, 2012, 21 (6): 1230-1247). However, clinical development of these approaches depends on the resolution of many general problems in the field of gene and protein replacement therapy, such as delivery to the multiple organs and cell types affected in FRDA patients, and, for gene therapy, other potential problems including controlled expression, immunogenicity and genotoxicity (Gonzalez-Cabo et al., Adv Exp Med Biol, 2009, 652:247-261: Soragni and Gottesfeld, Expert Opin Orphan Drugs. 2016, 4 (9): 961-970). Recently, there has been considerable enthusiasm for development of therapeutic antisense oligonucleotides (ASOs), based largely on the success of intrathecal administration of the ASO nusinersen (also called Spinraza) to treat spinal muscular atrophy, a central nervous system (CNS) disease (Maharshi and Hasan, Clin Drug Investig, 2017, 37 (9): 807-817). In this regard, ASOs directed against the GAA·TTC repeats in the mutant FXN gene have been shown to upregulate mutant FXN expression in cultured cells (Li et al., Nucleic Acid Ther, 2018, 28 (1): 23-33), suggesting a potential therapeutic approach. In addition, a recent study described a "synthetic transcription factor" that could bind to the GAA·TTC repeats and upregulate mutant FXN expression in cultured cells (Caldarella et al., Int J Qual Health Care, 2012, 24 (4): 441-418). However, whether this synthetic transcription factor or its derivatives have sufficient drug-like properties to be developed into a therapeutic is completely unknown.

Methods of Treatment

The methods described herein include methods for the treatment of disorders associated with mutations in the FXN gene and/or that have reduced expression of frataxin protein (but wherein the frataxin protein itself is functional). In some embodiments, the disorder is Friedreich ataxia (FRDA). Generally, the methods include administering a therapeutically effective amount of an agent that increases levels of frataxin protein as described herein, to a subject who is in need of, or who has been determined to be in need of, such treatment. Methods known in the art can be used to diagnose or identify a subject as having a disorder associated with a mutation in the FXN gene that reduces expression of the frataxin protein, e.g., sequencing or identification of the presence of trinucleotide repeat expansion (e.g., using a commercially available assay such as the Friedreich ataxia (FXN) Repeat Expansion Test (Athena Diagnostics)): a quantitative immunoassay to measure frataxin levels, e.g., as described in Plasterer et al., PLOS One. 2013; 8 (5):e63958, or a lateral flow test as described in Willis et al., Mol Genet Metab. 2008 August; 94 (4); 491-497 or commercially available kits such as the dipstick kit from abcam (ab109881); MRI to detect atrophy of the cervical spinal cord with minimal evidence of cerebellar atrophy: transcranial sonography for assessment of both cerebellar and non-cerebellar abnormalities, e.g., dentate hyperechogenicity. Typically, subjects present with gait ataxia (e.g., tabetocerebellar gait), with ataxia progressing to the legs, trunk, and arms; development of tremors; titubation; and trembling. To determine severity, any of three scales can be used, e.g., The International Cooperative Ataxia Rating Scale (ICARS), the Friedreich Ataxia Rating Scale (FARS), and the Scale for the Assessment and Rating of Ataxia (SARA), see, e.g., Bürk et al., J. Neurochem. 126 Suppl. 1:118-24 (2013).

As used in this context, to "treat" means to ameliorate at least one symptom of the disorder associated with mutations in the FXN gene that reduce expression. FRDA is an autosomal recessive neurodegenerative disorder that results in progressive gait and limb ataxia with associated limb muscle weakness, absent lower limb reflexes, extensor plantar responses, dysarthria, and decreased vibratory sense and proprioception, as well as cardiac manifestations including cardiac dysfunction and heart failure: visual field defects; and diabetes. Thus, a treatment can result in a reduction in the severity of these deficits or a reduction in the rate of decline or degeneration. Administration of a therapeutically effective amount of a compound described herein for the treatment of a condition associated with mutations in the FXN gene that reduce expression, e.g., FRDA, will result in improvement in one or more symptoms, e.g., reduction in the severity or rate of decline in gait and limb ataxia, limb muscle weakness, deficits in lower limb reflexes, extensor plantar responses, dysarthria, and vibratory sense and proprioception, and a return or approach to normal gait and limb movements, a return or approach to normal muscle strength and reflexes, a return or approach to normal (flexor) plantar responses, reduced dysarthria/improved speech, and a return or approach to normal vibratory sense and proprioception, as well as a reduction in the severity or risk of cardiac dysfunction and/or heart failure or diabetes. In some embodiments, the treatment upregulates mutant FXN and ameliorates disease symptoms (e.g., motor coordination defects, glucose/insulin intolerance, dorsal root ganglia histopathology, and mitochondrial dysfunction). In some embodiments, the treatment results in decreased morbidity or mortality, e.g., a delayed loss of ambulation, an increased life span (average age of death is 37.7+14.4 years, range 21-69, Harding et al., J. Med Genet. 18 (4): 285-7 (1981)) and/or an improved quality of life.

In some embodiments, the subject does not have glaucoma.

Therapeutic Agents

Agents that increase expression of frataxin protein as described herein include inhibitors of one or more protein kinases listed in Table A/Table 1: these factors are referred to herein as FXN Repressing Factors (FXN-RFs). In some embodiments, the FXN-RF is ROCK1 or ROCK2, and the inhibitor is an inhibitor of ROCK1, an inhibitor of ROCK2, or an inhibitor of both ROCK1/ROCK2 (also referred to herein as ROCK1/2). ROCK1 and ROCK2 are highly similar (about 65% identity at the protein level, see Defert and Boland, Expert Opin Ther Pat 27 507-515 (2017)) but their tissue distribution can vary.

The agents can include inhibitory nucleic acids, inhibitory proteins or peptides, and small molecule inhibitors.

Small Molecule Inhibitors of FXN-RF's

A number of small molecule inhibitors of FXN-RFs are known in the art, including inhibitors of ROCK1/2, many of which are commercially available. For example, the following small molecule inhibitors of ROCK1/2 can be used: cyclohexanecarboxamides such as Y-27632 ((+)-(R)-trans-4-(1-aminoethyl)-N-(4-pyridyl)cyclohexanecarboxamide dihydrochloride) and Y-30131 ((+)-(R)-trans-4-(1-aminoethyl)-N-(1H-pyrrolo[2, 3-b]pyridin-4-yl)cyclohexanecarboxamide dihydrochloride) (see Ishizaki et al., Mol Pharmacol. 2000 May: 57 (5): 976-83); dihydropyrimidinones and dihydropyrimidines, e.g., bicyclic dihydropyrimidine-carboxamides (such as those described in Sehon et al. J. Med. Chem., 2008, 51 (21): 6631-6634 and US2018/0170939); ureidobenzamides such as CAY10622 (3-[[[[[4-(aminocarbonyl)phenyl]amino]carbonyl]amino]methyl]-N-(1, 2, 3, 4-tetrahydro-7-isoquinolinyl)-benzamide); Thiazovivin; GSK429286A; RKI-1447 (1-(3-Hydroxy benzyl)-3-(4-(pyridin-4-yl)thiazol-2-yl)urea); GSK180736A (GSK180736); Hydroxyfasudil (HA-1100); OXA 06; Y-39983; Netarsudil (AR-13324, see Lin et al., J Ocul Pharmacol Ther. 2018 Mar. 1; 34 (1-2): 40-51, U.S. Pat. Nos. 8,450,344 and 8,394,826); GSK269962/GSK269962A; Fasudil (HA-1077, 1-(5-isoquinolinesulfonyl)-homopiperazine) and its derivatives such Ripasudil (K-115, 4-fluoro-5-[[(2S)-2-methyl-1,4-diazepan-1-yl]sulfonyl]isoquinoline; see WO1999/20620) and others that share the core structure of 5-(1,4-diazepan-1-ylsulfonyl) isoquinoline; KD025 (SLx-2119) and related compound and XD-4000 (see, e.g. Liao et al. 2007 J Cardiovasc Pharmacol 50:17-24; WO2010/104851 US 2012/0202793); SR 3677; AS 1892802; H-1152 ((S)-(+)-2-Methyl-1-[(4-methyl-5-isoquinolinyl)sulfonyl] homopiperazine, Ikenoya et al., J. Neurochem. 81:9, 2002; Sasaki et al., Pharmacol. Ther. 93:225, 2002); N-(4-Pyridyl)-N'-(2,4,6-trichlorophenyl) urea (Takami et al., Bioorg. Med. Chem. 12:2115, 2004); and 3-(4-Pyridyl)-1H-indole (Yarrow et al., Chem. Biol. 12:385, 2005); 3-[2-(aminomethyl)-5-[(pyridin-4-yl)carbamoyl]phenyl]benzo-ates including AMA0076 (compound 32, Boland et al., Bioorganic & Medicinal Chemistry Letters 23 (23): 6442-6446 (2013)) TC-S 7001 and AT13148, and pharmaceutically acceptable salts thereof. Inhibitors with the scaffold 4-Phenyl-1H-pyrrolo[2,3-b]pyridine, including compound TS-f22, are described in Shen et al., Scientific Reports 5:16749 (2015). Other ROCK1/2 inhibitors include isoquinoline sulfonyl derivatives disclosed in WO 97/23222, Nature 389, 990-994 (1997) and WO 99/64011; heterocyclic amino derivatives disclosed in WO 01/56988; indazole derivatives disclosed in WO 02/100833; pyridylthiazole urea and other ROCK1/2 inhibitors as described in 20170049760; and quinazoline derivatives disclosed in WO 02/076976 and WO 02/076977; in WO02053143, p. 7, lines 1-5, EP1163910 A1, p. 3-6, WO02076976 A2, p. 4-9, preferably the compounds described on p. 10-13 and p. 14 lines 1-3, WO02/076977A2, the compounds I-VI of p. 4-5, WO03/082808, p. 3-p. 10 (until line 14), the indazole derivatives described in U.S. Pat. No. 7,563,906 B2, WO2005074643A2, p. 4-5 and the specific compounds of p. 10-11, WO2008015001, pages 4-6, EP1256574, claims 1-3, EP1270570, claims 1-4, and EP 1 550 660. These inhibitors are generally commercially available, e.g., from Santa Cruz Biotechnology, Selleck Chemicals, and Tocris, among others. For example, fasudil and Hydroxy fasudil are obtainable from Asahi Kasei Pharma Corp (Asano et al., J Pharmcol Exp Ther, 1987, 241 (3): 1033-1040), Y-39983 is obtainable from Novartis/Senju (Fukiage et al., Biochem Biophys Res Commun, 2001, 288 (2): 296-300) and Y27632 is obtainable from Mitsubishi Pharma (Fu et al., FEBS Lett, 1998, 440 (1-2): 183-187). (S)-(+)-2-Methyl-1-[(4-methyl-5-isoquinolinyl) sulfonyl]homopiperazine], N-(4-Pyridyl)-N'-(2,4,6- trichlorophenyl) urea and 3-(4-Pyridyl)-1H-indole are also available at AXXORA (UK) Ltd and other suppliers. Additional small molecule Rho kinase inhibitors include those described in PCT Publication Nos. WO2013030216; WO2007042321A2; WO2008049919; WO2011023986A1; WO2011107608A1; WO2003059913, WO2003064397, WO2005003101, WO22004112719, WO 2009/155209; WO 2012/135697; WO 2005/003101; WO2003062225; WO 98/06433; and WO2003062227; U.S. Pat. Nos. 7,217,722; 7,199,147; 8,071,779; 8,093,266; 7,199,147; 6,369,087; 6,369,086; 6,372,733; 8,637,310; 9,174,939; 6,372,778B1; European Patents and applications 2628482, 1256578; 1270570; 1550660; EP0370498A2; and EP0721331A1; and U.S. Patent Application Publication Nos. 2016/0237095; 2015/0238601; 2014/0336440; 2014/0179689; 2013/0131106; 2012/0178752; 2011/0166104; 2010/0183604; 2010/0041645; 2008/0161297; 2012/0270868; 2009/0203678; 2010/0137324; 2013/0131059; 2003/0220357, 2006/0241127, 2005/0182040 and 2005/0197328. See also Tamura et al. Biophys Ada 2005 1754:245-252; Defert and Boland, Expert Opin Ther Pat 27 507-515 (2017); Pan et al., Drug Discovery Today 18 (23-24):1323-1333 (2013); Lin and Zheng, Expert Opinion on Drug Discovery, 10 (9):991-1010 (2015); and US20180110837.

Protein Peptide inhibitors

In some embodiments the inhibitor is a protein or peptide inhibitor of a FXN-RF as known in the art, including inhibitors of ROCK1/2, e.g., a peptide consisting of 4-30 residues and exhibiting the sequence YSPS (SEQ ID NO: 19), ERTYSPS (SEQ ID NO: 20), or ERTYSPSTAVRS (SEQ ID NO: 21) (see, e.g., US20170296617), or a kinase-defective mutant of ROCK1 or caspase 3 cleavage-resistant mutant of ROCK1 (e.g., as described in 2006/0142193). In some embodiments, the peptide further comprises one or more, e.g., all, D-amino acid residues.

Inhibitory Nucleic Acids

Inhibitory nucleic acids useful in the present methods and compositions include antisense oligonucleotides, ribozymes, external guide sequence (EGS) oligonucleotides, siRNA compounds, single- or double-stranded RNA interference (RNAi) compounds such as siRNA compounds, modified bases/locked nucleic acids (LNAs), peptide nucleic acids (PNAs), and other oligomeric compounds or oligonucleotide mimetics that specifically hybridize to at least a portion of a target nucleic acid and modulate its function. In some embodiments, the inhibitory nucleic acids include antisense RNA, antisense DNA, chimeric antisense oligonucleotides, antisense oligonucleotides comprising modified linkages, interference RNA (RNAi), short interfering RNA (siRNA): a micro, interfering RNA (miRNA); a small, temporal RNA (stRNA); or a short, hairpin RNA (shRNA): small RNA-induced gene activation (RNAa); small activating RNAs (saRNAs), or combinations thereof.

The following Table A provides exemplary mRNA target sequences for the FXN-RFs described herein:

TABLE A

| FXN REPRESSING FACTORS | | |
|---|---|---|
| Gene symbol | Gene name | NCBI RefSeq Acc. No.- Homo sapiens (nucleic acid) |
| AGK | acylglycerol kinase | NM_001364948.1 |
| PAN3 | poly(A) specific ribonuclease subunit | NM_175854.7 |
| PIP4K2C | phosphatidylinositol-5-phosphate 4-kinase type 2 gamma | NM_024779.4 (Var 1) NM_001146258.1 (Var 2) NM_001146259.1 (Var 3) NM_001146260.1 (Var 4) |
| PRKAR2B | protein kinase cAMP-dependent type II regulatory subunit beta | NM_002736.2 |
| RB1CC1 | RB1 inducible coiled-coil 1 | NM_014781.4 (Var 1) NM_001083617.1 (Var 2) |
| ROCK1 | rho associated coiled-coil containing protein kinase 1 | NM_005406.2 |
| ROCK2 | rho associated coiled-coil containing protein kinase 2 | NM_004850.4 (Var 1) NM_001321643.1 (Var 2) |
| TEX14 | testis expressed 14, intercellular bridge forming factor | NM_198393.3 (Var 1) NM_031272.4 (Var 2) NM_001201457.1 (Var 3) |
| ULK4 | unc-51 like kinase 4 | NM_017886.3 (Var 1) NM_001322500.1 (Var 2) NM_001322501.1 (Var 3) |

In some embodiments, the inhibitory nucleic acids are 10 to 50, 10 to 20, 10 to 25, 13 to 50, or 13 to 30 nucleotides in length. One having ordinary skill in the art will appreciate that this embodies inhibitory nucleic acids having complementary portions of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length, or any range therewithin. In some embodiments, the inhibitory nucleic acids are 15 nucleotides in length. In some embodiments, the inhibitory nucleic acids are 12 or 13 to 20, 25, or 30 nucleotides in length. One having ordinary skill in the art will appreciate that this embodies inhibitory nucleic acids having complementary portions of 12, 13, 14, 15, 16, 17, 18, 19, 20, 21, 22, 23, 24, 25, 26, 27, 28, 29 or 30 nucleotides in length, or any range therewithin (complementary portions refers to those portions of the inhibitory nucleic acids that are complementary to the target sequence).

The inhibitory nucleic acids useful in the present methods are sufficiently complementary to the target RNA, i.e., hybridize sufficiently well and with sufficient specificity, to give the desired effect. "Complementary" refers to the capacity for pairing, through hydrogen bonding, between two sequences comprising naturally or non-naturally occurring bases or analogs thereof. For example, if a base at one position of an inhibitory nucleic acid is capable of hydrogen bonding with a base at the corresponding position of a RNA, then the bases are considered to be complementary to each other at that position. 100% complementarity is not required. Routine methods can be used to design an inhibitory nucleic acid that binds to the target sequence with sufficient specificity. In some embodiments, the methods include using bioinformatics methods known in the art to identify regions of secondary structure, e.g., one, two, or more stem-loop structures, or pseudoknots, and selecting those regions to target with an inhibitory nucleic acid. For example, "gene walk" methods can be used to optimize the inhibitory activity of the nucleic acid; for example, a series of oligonucleotides of 10-30 nucleotides spanning the length of a target RNA can be prepared, followed by testing for activity. Optionally, gaps, e.g., of 5-10 nucleotides or more, can be left between the target sequences to reduce the number of oligonucleotides synthesized and tested. GC content is preferably between about 30-60%. Contiguous runs of three or more Gs or Cs should be avoided where possible (for example, it may not be possible with very short (e.g., about 9-10 nt) oligonucleotides).

In some embodiments, the inhibitory nucleic acid molecules can be designed to target a specific region of the RNA sequence. For example, a specific functional region can be targeted, e.g., a region comprising a known RNA localization motif (i.e., a region complementary to the target nucleic acid on which the RNA acts). Alternatively or in addition, highly conserved regions can be targeted, e.g., regions identified by aligning sequences from disparate species such as primate (e.g., human) and rodent (e.g., mouse) and looking for regions with high degrees of identity. Percent identity can be determined routinely using basic local alignment search tools (BLAST programs) (Altschul et al., J. Mol. Biol., 1990, 215, 403-410; Zhang and Madden, Genome Res., 1997, 7, 649-656), e.g., using the default parameters.

Once one or more target regions, segments or sites have been identified, e.g., within a target sequence known in the art or provided herein, inhibitory nucleic acid compounds are chosen that are sufficiently complementary to the target, i.e., that hybridize sufficiently well and with sufficient specificity (i.e., do not substantially bind to other non-target RNAs), to give the desired effect.

In the context of this invention, hybridization means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. Complementary, as used herein, refers to the capacity for precise pairing between two nucleotides. For example, if a nucleotide at a certain position of an oligonucleotide is capable of hydrogen bonding with a nucleotide at the same position of a RNA molecule, then the inhibitory nucleic acid and the RNA are considered to be complementary to each other at that position. The inhibitory nucleic acids and the RNA are complementary to each other when a sufficient number of corresponding positions in each molecule are occupied by nucleotides which can hydrogen bond with each other. Thus, "specifically hybridisable" and "complementary" are terms which are used to indicate a sufficient degree of complementarity or precise pairing such that stable and specific binding occurs between the inhibitory nucleic acid and the RNA target. For example, if a base at one position of an inhibitory nucleic acid is capable of hydrogen bonding with a base at the corresponding position of a RNA, then the bases are considered to be complementary to each other at that position. 100% complementarity is not required.

It is understood in the art that a complementary nucleic acid sequence need not be 100% complementary to that of its target nucleic acid to be specifically hybridisable. A complementary nucleic acid sequence for purposes of the present methods is specifically hybridisable when binding of the sequence to the target RNA molecule interferes with the normal function of the target RNA to cause a loss of activity, and there is a sufficient degree of complementarity to avoid non-specific binding of the sequence to non-target RNA sequences under conditions in which specific binding is desired. e.g., under physiological conditions in the case of in vivo assays or therapeutic treatment, and in the case of in vitro assays, under conditions in which the assays are performed under suitable conditions of stringency. For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., *Molecular Cloning: A Laboratory Manual*, Cold Spring Harbor Laboratory Press, New York.

In general, the inhibitory nucleic acids useful in the methods described herein have at least 80% sequence complementarity to a target region within the target nucleic acid, e.g., 90%, 95%, or 100% sequence complementarity to the target region within an RNA. For example, an antisense compound in which 18 of 20 nucleobases of the antisense oligonucleotide are complementary, and would therefore specifically hybridize, to a target region would represent 90 percent complementarity. Percent complementarity of an inhibitory nucleic acid with a region of a target nucleic acid can be determined routinely using basic local alignment search tools (BLAST programs) (Altschul et al., J. Mol. Biol., 1990, 215, 403-410; Zhang and Madden, Genome Res., 1997, 7, 649-656). Inhibitory nucleic acids that hybridize to an RNA can be identified through routine experimentation. In general, the inhibitory nucleic acids must retain specificity for their target, i.e., must not directly bind to, or directly significantly affect expression levels of, transcripts other than the intended target. For further disclosure regarding inhibitory nucleic acids, please see US2010/0317718 (antisense oligos); US2010/0249052 (double-stranded ribonucleic acid (dsRNA)); US2009/0181914 and US2010/0234451 (LNAs); US2007/0191294 (siRNA analogues); US2008/0249039 (modified siRNA); and WO2010/129746 and WO2010/040112 (inhibitory nucleic acids).

Antisense

In some embodiments, the inhibitory nucleic acids are antisense oligonucleotides. Antisense oligonucleotides are typically designed to block expression of a DNA or RNA target by binding to the target and halting expression at the level of transcription, translation, or splicing. Antisense oligonucleotides of the present invention are complementary nucleic acid sequences designed to hybridize under stringent conditions to an RNA. Thus, oligonucleotides are chosen that are sufficiently complementary to the target, i.e., that hybridize sufficiently well and with sufficient specificity, to give the desired effect.

siRNA shRNA

In some embodiments, the nucleic acid sequence that is complementary to a target RNA can be an interfering RNA, including but not limited to a small interfering RNA ("siRNA") or a small hairpin RNA ("shRNA"). Methods for constructing interfering RNAs are well known in the art. For example, the interfering RNA can be assembled from two separate oligonucleotides, where one strand is the sense strand and the other is the antisense strand, wherein the antisense and sense strands are self-complementary (i.e., each strand comprises nucleotide sequence that is complementary to nucleotide sequence in the other strand: such as where the antisense strand and sense strand form a duplex or double stranded structure); the antisense strand comprises nucleotide sequence that is complementary to a nucleotide sequence in a target nucleic acid molecule or a portion thereof (i.e., an undesired gene) and the sense strand comprises nucleotide sequence corresponding to the target nucleic acid sequence or a portion thereof. Alternatively, interfering RNA is assembled from a single oligonucleotide, where the self-complementary sense and antisense regions are linked by means of nucleic acid based or non-nucleic acid-based linker(s). The interfering RNA can be a polynucleotide with a duplex, asymmetric duplex, hairpin or asymmetric hairpin secondary structure, having self-complementary sense and antisense regions, wherein the antisense region comprises a nucleotide sequence that is complementary to nucleotide sequence in a separate target nucleic acid molecule or a portion thereof and the sense region having nucleotide sequence corresponding to the target nucleic acid sequence or a portion thereof. The interfering can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siRNA molecule capable of mediating RNA interference. In some embodiments, the interfering RNA coding region encodes a self-complementary RNA molecule having a sense region, an antisense region and a loop region. Such an RNA molecule when expressed desirably forms a "hairpin" structure, and is referred to herein as an "shRNA." The loop region is generally between about 2 and about 10 nucleotides in length. In some embodiments, the loop region is from about 6 to about 9 nucleotides in length. In some embodiments, the sense region and the antisense region are between about 15 and about 20 nucleotides in length. Following post-transcriptional processing, the small hairpin RNA is converted into a siRNA by a cleavage event mediated by the enzyme Dicer, which is a member of the RNase III family. The siRNA is then capable of inhibiting the expression of a gene with which it shares homology. For details, see Brummelkamp et al., Science 296:550-553, (2002); Lee et al, Nature Biotechnol., 20, 500-505, (2002); Miyagishi and Taira, Nature Biotechnol 20:497-500, (2002); Paddison et al. Genes & Dev. 16:948-958, (2002); Paul, Nature Biotechnol, 20, 505-508, (2002); Sui, Proc. Natl. Acad. Sd. USA, 99 (6), 5515-5520, (2002); Yu et al. Proc NatlAcadSci USA 99:6047-6052, (2002).

The target RNA cleavage reaction guided by siRNAs is highly sequence specific. In general, siRNA containing a nucleotide sequences identical to a portion of the target nucleic acid are preferred for inhibition. However, 100% sequence identity between the siRNA and the target gene is not required to practice the present invention. Thus the invention has the advantage of being able to tolerate sequence variations that might be expected due to genetic mutation, strain polymorphism, or evolutionary divergence. For example, siRNA sequences with insertions, deletions, and single point mutations relative to the target sequence have also been found to be effective for inhibition. Alternatively, siRNA sequences with nucleotide analog substitutions or insertions can be effective for inhibition. In general the siRNAs must retain specificity for their target, i.e., must not directly bind to, or directly significantly affect expression levels of, transcripts other than the intended target.

In some embodiments, the following validated ROCK1/2-specific siRNA molecules may be used: ON-TARGET PLUS siRNA human ROCK I (ID: L-003536-00; Dharmacon); ON-TARGET PLUS siRNA human ROCK II (ID: L-004610-00; Dharmacon).

The following Table B provides exemplary shRNA sequences targeting the FXN-RFs described herein:

TABLE B

SHRNAs TARGETING FXN REPRESSING FACTORS

| Gene symbol | Clone number | Full hairpin sequence (sense sequence in bold) | SEQ ID NO: |
|---|---|---|---|
| AGK | TRCN0000153540 | CCGGCCATTGAACTGTCCATCACAACTCGA GTTGTGATGGACAGTTCAATGGTTTTTG | 1 |

TABLE B-continued

SHRNAs TARGETING FXN REPRESSING FACTORS

| Gene symbol | Clone number | Full hairpin sequence (sense sequence in bold) | SEQ ID NO: |
|---|---|---|---|
| | TRCN0000153828 | CCGGCCTCAACTGTACTTGGAGAAACTCGAGTTTCTCCAAGTACAGTTGAGGTTTTTG | 2 |
| PAN3 | TRCN0000049806 | CCGGCGTTGCTTATATGCAACCGAACTCGAGTTCGGTTGCATATAAGCAACGTTTTG | 3 |
| | TRCN0000049805 | CCGGCGTTATCTGTTGAAACTCTTTCTCGAGAAAGAGTTTCAACAGATAACGTTTTG | 4 |
| PIP4K2C | TRCN0000037720 | CCGGCGCTTCCTTATCTCCTACGATCTCGAGATCGTAGGAGATAAGGAAGCGTTTTG | 5 |
| | TRCN0000037722 | CCGGCCTTACACAGTATGATGCCAACTCGAGTTGGCATCATACTGTGTAAGGTTTTG | 6 |
| PRKAR2B | TRCN0000037815 | CCGGCCTGAAAGTAGTAGATGTGATCTCGAGATCACATCTACTACTTTCAGGTTTTG | 7 |
| | TRCN0000037817 | CCGGGTCCAGGATTATACATCCAAACTCGAGTTTGGATGTATAATCCTGGACTTTTG | 8 |
| RB1CC1 | TRCN0000013524 | CCGGGCTGTGAATGAGTTTGTAATACTCGAGTATTACAAACTCATTCACAGCTTTTT | 9 |
| | TRCN0000013526 | CCGGGCAAAGAAATTAGGGAATCTTCTCGAGAAGATTCCCTAATTTCTTTGCTTTTT | 10 |
| ROCK1 (1) | TRCN0000121092 | CCGGCGGGTTGTTCAGATTGAGAAACTCGAGTTTCTCAATCTGAACAACCCGTTTTG | 11 |
| (2) | TRCN0000121095 | CCGGGCATTCCAAGATGATCGTTATCTCGAGATAACGATCATCTTGGAATGCTTTTG | 12 |
| (3) | TRCN0000121093 | CCGGGCACCAGTTGTACCCGATTTACTCGAGTAAATCGGGTACAACTGGTGCTTTTG | 13 |
| ROCK2 | TRCN0000000977 | CCGGCCTGTGTACCTGATGGAAGTTCTCGAGAACTTCCATCAGGTACACAGGTTTT | 14 |
| TEX14 | TRCN0000037472 | CCGGCCTACCAAGATTTCCAAGAATCTCGAGATTCTTGGAAATCTTGGTAGGTTTTG | 15 |
| | TRCN0000037471 | CCGGCCGAAACCTTACTATGATATTCTCGAGAATATCATAGTAAGGTTTCGGTTTTG | 16 |
| ULK4 | TRCN0000002204 | CCGGCAGGGCTTTATTACAGGAGAACTCGAGTTCTCCTGTAATAAAGCCCTGTTTTT | 17 |
| | TRCN0000002205 | CCGGCGACGGAAGGGAACAATCAATCTCGAGATTGATTGTTCCCTTCCGTCGTTTTT | 18 |

Ribozymes

Trans-cleaving enzymatic nucleic acid molecules can also be used: they have shown promise as therapeutic agents for human disease (Usman & McSwiggen, 1995 Ann. Rep. Med. Chem. 30, 285-294; Christoffersen and Marr, 1995 J. Med. Chem. 38, 2023-2037). Enzymatic nucleic acid molecules can be designed to cleave specific RNA targets within the background of cellular RNA. Such a cleavage event renders the RNA non-functional.

In general, enzymatic nucleic acids with RNA cleaving activity act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets. Several approaches such as in vitro selection (evolution) strategies (Orgel, 1979, Proc. R. Soc. London, B 205, 435) have been used to evolve new nucleic acid catalysts capable of catalyzing a variety of reactions, such as cleavage and ligation of phosphodiester linkages and amide linkages, (Joyce, 1989, Gene, 82, 83-87; Beaudry et al., 1992, Science 257, 635-641; Joyce, 1992, Scientific American 267, 90-97; Breaker et al, 1994, TIBTECH 12, 268; Bartel et al, 1993, Science 261:1411-1418; Szostak, 1993, TIBS 17, 89-93; Kumar et al, 1995, FASEB J., 9, 1183; Breaker, 1996, Curr. Op. Biotech., 1, 442). The development of ribozymes that are optimal for catalytic activity would contribute significantly to any strategy that employs RNA-cleaving ribozymes for the purpose of regulating gene expression. The hammerhead ribozyme, for example, functions with a catalytic rate (kcat) of about 1 min-1 in the presence of saturating (10 mM) concentrations of $Mg^{2+}$ cofactor. An artificial "RNA ligase" ribozyme has been shown to catalyze the corresponding self-modification reaction with a rate of about 100 $min^{-1}$. In addition, it is known that certain modified hammerhead ribozymes that have substrate binding arms made of DNA catalyze RNA cleavage with multiple turn-over rates that approach 100 $min^{-1}$.

Modified Inhibitory Nucleic Acids

In some embodiments, the inhibitory nucleic acids used in the methods described herein are modified, e.g., comprise one or more modified bonds or bases. A number of modified bases include phosphorothioate, methylphosphonate, peptide nucleic acids, or locked nucleic acid (LNA) molecules. Some inhibitory nucleic acids are fully modified, while others are chimeric and contain two or more chemically distinct regions, each made up of at least one nucleotide. These inhibitory nucleic acids typically contain at least one region of modified nucleotides that confers one or more beneficial properties (such as, for example, increased nuclease resistance, increased uptake into cells, increased binding affinity for the target) and a region that is a substrate for enzymes capable of cleaving RNA:DNA or RNA:RNA hybrids. Chimeric inhibitory nucleic acids of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures comprise, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference.

In some embodiments, the inhibitory nucleic acid comprises at least one nucleotide modified at the 2' position of the sugar, most preferably a 2'-O-alkyl, 2'-O-alkyl-O-alkyl or 2'-fluoro-modified nucleotide. In other preferred embodiments, RNA modifications include 2'-fluoro, 2'-amino and 2' O-methyl modifications on the ribose of pyrimidines, abasic residues or an inverted base at the 3' end of the RNA. Such modifications are routinely incorporated into oligonucleotides and these oligonucleotides have been shown to have a higher Tm (i.e., higher target binding affinity) than: 2'-deoxyoligonucleotides against a given target.

A number of nucleotide and nucleoside modifications have been shown to make the oligonucleotide into which they are incorporated more resistant to nuclease digestion than the native oligodeoxynucleotide: these modified oligos survive intact for a longer time than unmodified oligonucleotides. Specific examples of modified oligonucleotides include those comprising modified backbones, for example, phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioate backbones and those with heteroatom backbones, particularly CH$_2$—NH—O—CH$_2$, CH, ~N(CH$_3$)~O~CH$_2$ (known as a methylene(methylimino) or MMI backbone], CH$_2$—O—N(CH$_3$)—CH$_2$, CH$_2$—N(CH$_3$)—N(CH$_3$)—CH$_2$ and O—N(CH$_3$)—CH$_2$—CH$_2$ backbones, wherein the native phosphodiester backbone is represented as O—P—O—CH); amide backbones (see De Mesmaeker et al. Ace. Chem. Res. 1995, 28:366-374); morpholino backbone structures (see Summerton and Weller, U.S. Pat. No. 5,034,506); peptide nucleic acid (PNA) backbone (wherein the phosphodiester backbone of the oligonucleotide is replaced with a polyamide backbone, the nucleotides being bound directly or indirectly to the aza nitrogen atoms of the polyamide backbone, see Nielsen et al., Science 1991, 254, 1497). Phosphorus-containing linkages include, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2': see U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

Morpholino-based oligomeric compounds are described in Dwaine A. Braasch and David R. Corey, Biochemistry, 2002, 41 (14), 4503-4510); Genesis, volume 30, issue 3, 2001; Heasman, J., Dev. Biol., 2002, 243, 209-214; Nasevicius et al., Nat. Genet., 2000, 26, 216-220; Lacerra et al., Proc. Natl. Acad. Sci., 2000, 97, 9591-9596; and U.S. Pat. No. 5,034,506, issued Jul. 23, 1991.

Cyclohexenyl nucleic acid oligonucleotide mimetics are described in Wang et al., J. Am. Chem. Soc., 2000, 122, 8595-8602.

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts: see U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

One or more substituted sugar moieties can also be included, e.g., one of the following at the 2' position; OH, SH, SCH$_3$, F, OCN, OCH$_3$OCH$_3$, OCH$_3$O(CH$_2$)n CH$_3$, O(CH$_2$)n NH$_2$ or O(CH$_2$)n CH$_3$ where n is from 1 to about 10; Ci to C10 lower alkyl, alkoxyalkoxy, substituted lower alkyl, alkaryl or aralkyl; Cl; Br; CN; CF3; OCF3; O-, S-, or N-alkyl; O-, S-, or N-alkenyl; SOCH3; SO2 CH3; ONO2; N3; NH2; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A preferred modification includes 2'-methoxyethoxy [2'-0-CH$_2$CH$_2$OCH$_3$, also known as 2'-O-(2-methoxyethyl)] (Martin et al, Helv. Chim. Acta, 1995, 78, 486). Other preferred modifications include 2'-methoxy (2'-0-CH$_3$), 2'-propoxy (2'-OCH$_2$CH$_2$CH$_3$) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

Inhibitory nucleic acids can also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxy methylcytosine (HMC), glycosyl HMC and gentobiosyl HMC, as well as synthetic nucleobases, e.g., 2-aminoadenine, 2-(methylamino) adenine, 2-(imidazolylalkyl) adenine, 2-(aminoalklyamino) adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl) adenine and 2,6-diaminopurine. Kornberg. A., DNA Replication, W. H. Freeman & Co., San Francisco, 1980, pp 75-77; Gebeyehu, G., et al. Nucl. Acids Res. 1987, 15:4513). A "universal" base known in the art, e.g., inosine, can also be included. 5-Me-C substitutions have been shown to increase nucleic acid duplex stability by 0.6-1.2<0>C. (Sanghvi, Y. S., in Crooke, S. T. and Lebleu, B., eds., Antisense Research and Applications, CRC Press, Boca Raton, 1993, pp. 276-278) and are presently preferred base substitutions.

It is not necessary for all positions in a given oligonucleotide to be uniformly modified, and in fact more than one of the aforementioned modifications may be incorporated in a single oligonucleotide or even at within a single nucleoside within an oligonucleotide.

In some embodiments, both a sugar and an internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, for example, an aminoethylglycine backbone. The nucleobases are retained and are bound directly or indirectly to aza nitrogen atoms of the amide portion of the backbone. Representative United States patents that teach the preparation of PNA compounds comprise, but are not limited to, U.S. Pat. Nos. 5,539,082; 5,714,331; and 5,719,262, each of which is herein incorporated by reference. Further teaching of PNA compounds can be found in Nielsen et al, Science, 1991, 254, 1497-1500.

Inhibitory nucleic acids can also include one or more nucleobase (often referred to in the art simply as "base") modifications or substitutions. As used herein, "unmodified" or "natural" nucleobases comprise the purine bases adenine (A) and guanine (G), and the pyrimidine bases thymine (T), cytosine (C) and uracil (U). Modified nucleobases comprise other synthetic and natural nucleobases such as 5-methylcytosine (5-me-C), 5-hydroxy methyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine and 3-deazaguanine and 3-deazaadenine.

Further, nucleobases comprise those disclosed in U.S. Pat. No. 3,687,808, those disclosed in 'The Concise Encyclopedia of Polymer Science and Engineering', pages 858-859, Kroschwitz, J. I., ed. John Wiley & Sons, 1990, those disclosed by Englisch et al., Angewandle Chemie, International Edition', 1991, 30, page 613, and those disclosed by Sanghvi, Y. S., Chapter 15, Antisense Research and Applications', pages 289-302, Crooke, S. T. and Lebleu, B. ea., CRC Press, 1993. Certain of these nucleobases are particularly useful for increasing the binding affinity of the oligomeric compounds of the invention. These include 5-substituted pyrimidines, 6-azapyrimidines and N-2, N-6 and 0-6 substituted purines, comprising 2-aminopropyladenine, 5-propynyluracil and 5-propynylcytosine. 5-methylcytosine substitutions have been shown to increase nucleic acid duplex stability by 0.6-1.2<0>C (Sanghvi, Y. S., Crooke, S. T. and Lebleu, B., eds, 'Antisense Research and Applications', CRC Press, Boca Raton, 1993, pp. 276-278) and are presently preferred base substitutions, even more particularly when combined with 2'-O-methoxyethyl sugar modifications. Modified nucleobases are described in U.S. Pat. No. 3,687,808, as well as U.S. Pat. Nos. 4,845,205; 5,130, 302; 5,134,066; 5,175,273; 5,367,066; 5,432,272; 5,457, 187; 5,459,255; 5,484,908; 5,502,177; 5,525,711; 5,552, 540; 5,587,469; 5,596,091; 5,614,617; 5,750,692, and 5,681,941, each of which is herein incorporated by reference.

In some embodiments, the inhibitory nucleic acids are chemically linked to one or more moieties or conjugates that enhance the activity, cellular distribution, or cellular uptake of the oligonucleotide. Such moieties comprise but are not limited to, lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al, Ann. N. Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Mancharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-t oxy-cholesterol moiety (Crooke et al., J. Pharmacol. Exp. Ther., 1996, 277, 923-937). See also U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463;

5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application No. PCT/US92/09196, filed Oct. 23, 1992, and U.S. Pat. No. 6,287,860, which are incorporated herein by reference. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxy cholesterol moiety. See, e.g., U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

Locked Nucleic Acids (LNAs)

In some embodiments, the modified inhibitory nucleic acids used in the methods described herein comprise locked nucleic acid (LNA) molecules, e.g., including [alpha]-L-LNAs. LNAs comprise ribonucleic acid analogues wherein the ribose ring is "locked" by a methylene bridge between the 2'-oxygen and the 4'-carbon—i.e., oligonucleotides containing at least one LNA monomer, that is, one 2'-0,4'-C-methylene-ß-D-ribofuranosyl nucleotide. LNA bases form standard Watson-Crick base pairs but the locked configuration increases the rate and stability of the basepairing reaction (Jepsen et al., Oligonucleotides, 14, 130-146 (2004)). LNAs also have increased affinity to base pair with RNA as compared to DNA. These properties render LNAs especially useful as probes for fluorescence in situ hybridization (FISH) and comparative genomic hybridization, as knockdown tools for miRNAs, and as antisense oligonucleotides to target mRNAs or other RNAs, e.g., RNAs as described herien.

The LNA molecules can include molecules comprising 10-30, e.g., 12-24, e.g., 12, 13, 14, 15, 16, 17, 18, 19, 20, 21, 22, 23, 24, 25, 26, 27, 28, 29, or 30 nucleotides in each strand, wherein one of the strands is substantially identical, e.g., at least 80% (or more, e.g., 85%, 90%, 95%, or 100%) identical, e.g., having 3, 2, 1, or 0 mismatched nucleotide(s), to a target region in the RNA. The LNA molecules can be chemically synthesized using methods known in the art.

The LNA molecules can be designed using any method known in the art: a number of algorithms are known, and are commercially available (e.g., on the internet, for example at exiqon.com). See, e.g., You et al., Nuc. Acids. Res. 34: e60 (2006); McTigue et al., Biochemistry 43:5388-405 (2004); and Levin et al., Nuc. Acids. Res. 34: e142 (2006). For example, "gene walk" methods, similar to those used to design antisense oligos, can be used to optimize the inhibitory activity of the LNA; for example, a series of oligonucleotides of 10-30 nucleotides spanning the length of a target RNA can be prepared, followed by testing for activity. Optionally, gaps, e.g., of 5-10 nucleotides or more, can be left between the LNAs to reduce the number of oligonucleotides synthesized and tested. GC content is preferably between about 30-60%. General guidelines for designing LNAs are known in the art; for example, LNA sequences will bind very tightly to other LNA sequences, so it is preferable to avoid significant complementarity within an LNA. Contiguous runs of more than four LNA residues, should be avoided where possible (for example, it may not be possible with very short (e.g., about 9-10 nt) oligonucleotides). In some embodiments, the LNAs are xylo-LNAs.

For additional information regarding LNAs see U.S. Pat. Nos. 6,268,490; 6,734,291; 6,770,748; 6,794,499; 7,034,133; 7,053,207; 7,060,809; 7,084,125; and 7,572,582; and U.S. Pre-Grant Pub. Nos. 20100267018:20100261175; and 20100035968: Koshkin et al. Tetrahedron 54, 3607-3630 (1998); Obika et al. Tetrahedron Lett. 39, 5401-5404 (1998); Jepsen et al., Oligonucleotides 14:130-146 (2004); Kauppinen et al., Drug Disc. Today 2 (3):287-290 (2005); and Ponting et al., Cell 136 (4):629-641 (2009), and references cited therein.

Making and Using Inhibitory Nucleic Acids

The nucleic acid sequences used to practice the methods described herein, whether RNA, cDNA, genomic DNA, vectors, viruses or hybrids thereof, can be isolated from a variety of sources, genetically engineered, amplified, and/or expressed/generated recombinantly. Recombinant nucleic acid sequences can be individually isolated or cloned and tested for a desired activity. Any recombinant expression system can be used, including e.g. in vitro, bacterial, fungal, mammalian, yeast, insect or plant cell expression systems.

Nucleic acid sequences of the invention can be inserted into delivery vectors and expressed from transcription units within the vectors. The recombinant vectors can be DNA plasmids or viral vectors. Generation of the vector construct can be accomplished using any suitable genetic engineering techniques well known in the art, including, without limitation, the standard techniques of PCR, oligonucleotide synthesis, restriction endonuclease digestion, ligation, transformation, plasmid purification, and DNA sequencing, for example as described in Sambrook et al. Molecular Cloning: A Laboratory Manual. (1989)), Coffin et al. (Retroviruses. (1997)) and "RNA Viruses: A Practical Approach" (Alan J. Cann, Ed., Oxford University Press, (2000)). As will be apparent to one of ordinary skill in the art, a variety of suitable vectors are available for transferring nucleic acids of the invention into cells. The selection of an appropriate vector to deliver nucleic acids and optimization of the conditions for insertion of the selected expression vector into the cell, are within the scope of one of ordinary skill in the art without the need for undue experimentation. Viral vectors comprise a nucleotide sequence having sequences for the production of recombinant virus in a packaging cell. Viral vectors expressing nucleic acids of the invention can be constructed based on viral backbones including, but not limited to, a retrovirus, lentivirus, adenovirus, adeno-associated virus, pox virus or alphavirus. The recombinant vectors capable of expressing the nucleic acids of the invention can be delivered as described herein, and persist in target cells (e.g., stable transformants).

Nucleic acid sequences used to practice this invention can be synthesized in vitro by well-known chemical synthesis techniques, as described in, e.g., Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066.

Nucleic acid sequences of the invention can be stabilized against nucleolytic degradation such as by the incorporation of a modification, e.g., a nucleotide modification. For example, nucleic acid sequences of the invention includes a phosphorothioate at least the first, second, or third internucleotide linkage at the 5' or 3' end of the nucleotide sequence. As another example, the nucleic acid sequence can include a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O—NMA). As another example, the nucleic acid sequence can include at least one 2'-O-methyl-modified nucleotide, and in some embodiments, all of the nucleotides include a 2'-O-methyl modification. In some embodiments, the nucleic acids are "locked," i.e., comprise nucleic acid analogues in which the ribose ring is "locked" by a methylene bridge connecting the 2'-O atom and the 4'-C atom (see, e.g., Kaupinnen et al., Drug Disc. Today 2 (3): 287-290 (2005): Koshkin et al., J. Am. Chem. Soc., 120 (50): 13252-13253 (1998)). For additional modifications see US20100004320, US20090298916, and US20090143326.

Techniques for the manipulation of nucleic acids used to practice this invention, such as, e.g., subcloning, labeling probes (e.g., random-primer labeling using Klenow polymerase, nick translation, amplification), sequencing, hybridization and the like are well described in the scientific and patent literature, see, e.g., Sambrook et al., *Molecular Cloning: A Laboratory Manual* 3d ed. (2001); *Current Protocols in Molecular Biology*, Ausubel et al., eds. (John Wiley & Sons, Inc., New York 2010); Kriegler, Gene *Transfer and Expression: A Laboratory Manual* (1990): *Laboratory Techniques In Biochemistry And Molecular Biology: Hybridization With Nucleic Acid Probes, Part I. Theory and Nucleic Acid Preparation*. Tijssen, ed. Elsevier, N.Y. (1993).

Pharmaceutical Compositions

The methods described herein can include the administration of pharmaceutical compositions and formulations comprising inhibitory nucleic acid sequences designed to target an RNA.

In some embodiments, the compositions are formulated with a pharmaceutically acceptable carrier. The pharmaceutical compositions and formulations can be administered parenterally, topically, orally or by local administration, such as by aerosol or transdermally. The pharmaceutical compositions can be formulated in any way and can be administered in a variety of unit dosage forms depending upon the condition or disease and the degree of illness, the general medical condition of each patient, the resulting preferred method of administration and the like. Details on techniques for formulation and administration of pharmaceuticals are well described in the scientific and patent literature, see, e.g., *Remington: The Science and Practice of Pharmacy*, 21st ed., 2005.

The inhibitory nucleic acids can be administered alone or as a component of a pharmaceutical formulation (composition). The compounds may be formulated for administration, in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Formulations of the compositions of the invention include those suitable for intradermal, inhalation, oral/nasal, topical, parenteral, rectal, and/or intravaginal administration. The formulations may conveniently be presented in unit dosage form and may be prepared by any methods well known in the art of pharmacy. The amount of active ingredient (e.g., nucleic acid sequences of this invention) which can be combined with a carrier material to produce a single dosage form will vary depending upon the host being treated, the particular mode of administration, e.g., intradermal or inhalation. The amount of active ingredient which can be combined with a carrier material to produce a single dosage form will generally be that amount of the compound which produces a therapeutic effect, e.g., an antigen specific T cell or humoral response.

Pharmaceutical formulations can be prepared according to any method known to the art for the manufacture of pharmaceuticals. Such drugs can contain sweetening agents, flavoring agents, coloring agents and preserving agents. A formulation can be admixtured with nontoxic pharmaceutically acceptable excipients which are suitable for manufacture. Formulations may comprise one or more diluents, emulsifiers, preservatives, buffers, excipients, etc. and may be provided in such forms as liquids, powders, emulsions, lyophilized powders, sprays, creams, lotions, controlled release formulations, tablets, pills, gels, on patches, in implants, etc.

Pharmaceutical formulations for oral administration can be formulated using pharmaceutically acceptable carriers well known in the art in appropriate and suitable dosages. Such carriers enable the pharmaceuticals to be formulated in unit dosage forms as tablets, pills, powder, dragees, capsules, liquids, lozenges, gels, syrups, slurries, suspensions, etc., suitable for ingestion by the patient. Pharmaceutical preparations for oral use can be formulated as a solid excipient, optionally grinding a resulting mixture, and processing the mixture of granules, after adding suitable additional compounds, if desired, to obtain tablets or dragee cores. Suitable solid excipients are carbohydrate or protein fillers include, e.g., sugars, including lactose, sucrose, mannitol, or sorbitol; starch from corn, wheat, rice, potato, or other plants; cellulose such as methyl cellulose, hydroxypropylmethyl-cellulose, or sodium carboxy-methylcellulose; and gums including arabic and tragacanth; and proteins, e.g., gelatin and collagen. Disintegrating or solubilizing agents may be added, such as the cross-linked polyvinyl pyrrolidone, agar, alginic acid, or a salt thereof, such as sodium alginate. Push-fit capsules can contain active agents mixed with a filler or binders such as lactose or starches, lubricants such as talc or magnesium stearate, and, optionally, stabilizers. In soft capsules, the active agents can be dissolved or suspended in suitable liquids, such as fatty oils, liquid paraffin, or liquid polyethylene glycol with or without stabilizers.

Aqueous suspensions can contain an active agent (e.g., nucleic acid sequences of the invention) in admixture with excipients suitable for the manufacture of aqueous suspensions, e.g., for aqueous intradermal injections. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxy benzoate, one or more coloring agents, one or more flavoring agents and one or more sweetening agents, such as sucrose, aspartame or saccharin. Formulations can be adjusted for osmolarity.

In some embodiments, oil-based pharmaceuticals are used for administration of nucleic acid sequences of the invention. Oil-based suspensions can be formulated by suspending an active agent in a vegetable oil, such as arachis oil, olive oil, sesame oil or coconut oil, or in a mineral oil such as liquid paraffin; or a mixture of these. See e.g., U.S. Pat. No. 5,716,928 describing using essential oils or essential oil components for increasing bioavailability and reducing inter- and intra-individual variability of orally administered hydrophobic pharmaceutical compounds (see also U.S. Pat. No. 5,858,401). The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto (1997) J. Pharmacol. Exp. Ther. 281:93-102.

Pharmaceutical formulations can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soy bean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent. In alternative embodiments, these injectable oil-in-water emulsions of the invention comprise a paraffin oil, a sorbitan monooleate, an ethoxylated sorbitan monooleate and/or an ethoxylated sorbitan trioleate.

The pharmaceutical compounds can also be administered by in intranasal, intraocular and intravaginal routes including suppositories, insufflation, powders and aerosol formulations (for examples of steroid inhalants, see e.g., Rohatagi (1995) J. Clin. Pharmacol. 35:1187-1193; Tjwa (1995) Ann. Allergy Asthma Immunol. 75:107-111). Suppositories formulations can be prepared by mixing the drug with a suitable non-irritating excipient which is solid at ordinary temperatures but liquid at body temperatures and will therefore melt in the body to release the drug. Such materials are cocoa butter and polyethylene glycols.

In some embodiments, the pharmaceutical compounds can be delivered transdermally, by a topical route, formulated as applicator sticks, solutions, suspensions, emulsions, gels, creams, ointments, pastes, jellies, paints, powders, and aerosols.

In some embodiments, the pharmaceutical compounds can also be delivered as microspheres for slow release in the body. For example, microspheres can be administered via intradermal injection of drug which slowly release subcutaneously; see Rao (1995) J. Biomater. Sci. Polym. Ed. 7:623-645; as biodegradable and injectable gel formulations, see, e.g., Gao (1995) Pharm. Res. 12:857-863 (1995); or, as microspheres for oral administration, see, e.g., Eyles (1997) J. Pharm. Pharmacol. 49:669-674.

In some embodiments, the pharmaceutical compounds can be parenterally administered, such as by intravenous (IV) administration or administration into a body cavity or lumen of an organ. These formulations can comprise a solution of active agent dissolved in a pharmaceutically acceptable carrier. Acceptable vehicles and solvents that can be employed are water and Ringer's solution, an isotonic sodium chloride. In addition, sterile fixed oils can be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of active agent in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated using those suitable dispersing or wetting agents and suspending agents. The sterile injectable preparation can also be a suspension in a nontoxic parenterally-acceptable diluent or solvent, such as a solution of 1,3-butanediol. The administration can be by bolus or continuous infusion (e.g., substantially uninterrupted introduction into a blood vessel for a specified period of time).

In some embodiments, the pharmaceutical compounds and formulations can be lyophilized. Stable lyophilized formulations comprising an inhibitory nucleic acid can be made by lyophilizing a solution comprising a pharmaceutical of the invention and a bulking agent, e.g., mannitol, trehalose, raffinose, and sucrose or mixtures thereof. A process for preparing a stable lyophilized formulation can include lyophilizing a solution about 2.5 mg/mL protein, about 15 mg/mL sucrose, about 19 mg/mL NaCl, and a sodium citrate buffer having a pH greater than 5.5 but less than 6.5. See, e.g., US20040028670.

The compositions and formulations can be delivered by the use of liposomes. By using liposomes, particularly where the liposome surface carries ligands specific for target cells, or are otherwise preferentially directed to a specific organ, one can focus the delivery of the active agent into target cells in vivo. See, e.g., U.S. Pat. Nos. 6,063,400; 6,007,839; Al-Muhammed (1996) J. Microencapsul. 13:293-306; Chonn (1995) Curr. Opin. Biotechnol. 6:698-708; Ostro (1989) Am. J. Hosp. Pharm. 46:1576-1587. As used in the present invention, the term "liposome" means a vesicle composed of amphiphilic lipids arranged in a bilayer or bilayers. Liposomes are unilamellar or multilamellar vesicles that have a membrane formed from a lipophilic material and an aqueous interior that contains the composition to be delivered. Cationic liposomes are positively charged liposomes that are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes can also include "sterically stabilized" liposomes, i.e., liposomes comprising one or more specialized lipids. When incorporated into liposomes, these specialized lipids result in liposomes with enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860.

The formulations of the invention can be administered for prophylactic and/or therapeutic treatments. In some embodiments, for therapeutic applications, compositions are administered to a subject who is need of reduced triglyceride levels, or who is at risk of or has a disorder described herein, in an amount sufficient to cure, alleviate or partially arrest the clinical manifestations of the disorder or its complications: this can be called a therapeutically effective amount. For example, in some embodiments, pharmaceutical compositions of the invention are administered in an amount sufficient to decrease serum levels of triglycerides in the subject.

The amount of pharmaceutical composition adequate to accomplish this is a therapeutically effective dose. The dosage schedule and amounts effective for this use, i.e., the dosing regimen, will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the active agents' rate of absorption, bioavailability, metabolism, clearance, and the like (see, e.g., Hidalgo-Aragones (1996) J. Steroid Biochem. Mol. Biol. 58:611-617: Groning (1996) Pharmazie 51:337-341: Fotherby (1996) Contraception 54:59-69: Johnson (1995) J. Pharm. Sci. 84:1144-1146; Rohatagi (1995) Pharmazie 50:610-613: Brophy (1983) Eur. J. Clin. Pharmacol. 24:103-108: *Remington: The Science and Practice of Pharmacy*, 21st ed., 2005). The state of the art allows the clinician to determine the dosage regimen for each individual patient, active agent and disease or condition treated. Guidelines provided for similar compositions used as pharmaceuticals can be used as guidance to determine the dosage regiment, i.e., dose schedule and dosage levels, administered practicing the methods of the invention are correct and appropriate.

Single or multiple administrations of formulations can be given depending on for example: the dosage and frequency as required and tolerated by the patient, the degree and amount of therapeutic effect generated after each administration (e.g., effect on tumor size or growth), and the like. The formulations should provide a sufficient quantity of active agent to effectively treat, prevent or ameliorate conditions, diseases or symptoms.

In alternative embodiments, pharmaceutical formulations for oral administration are in a daily amount of between about 1 to 100 or more mg per kilogram of body weight per day. Lower dosages can be used, in contrast to administration orally, into the blood stream, into a body cavity or into a lumen of an organ. Substantially higher dosages can be used in topical or oral administration or administering by powders, spray or inhalation. Actual methods for preparing parenterally or non-parenterally administrable formulations will be known or apparent to those skilled in the art and are described in more detail in such publications as *Remington: The Science and Practice of Pharmacy*, 21st ed., 2005.

Various studies have reported successful mammalian dosing using complementary nucleic acid sequences. For example, Esau C., et al., (2006) Cell Metabolism, 3 (2): 87-98 reported dosing of normal mice with intraperitoneal doses of miR-122 antisense oligonucleotide ranging from 12.5 to 75 mg/kg twice weekly for 4 weeks. The mice appeared healthy and normal at the end of treatment, with no loss of body weight or reduced food intake. Plasma transaminase levels were in the normal range (AST ¾ 45, ALT ¾ 35) for all doses with the exception of the 75 mg/kg dose of miR-122 ASO, which showed a very mild increase in ALT and AST levels. They concluded that 50 mg/kg was an effective, non-toxic dose. Another study by Krützfeldt J., et al., (2005) Nature 438, 685-689, injected anatgomirs to silence miR-122 in mice using a total dose of 80, 160 or 240 mg per kg body weight. The highest dose resulted in a complete loss of miR-122 signal. In yet another study, locked nucleic acids ("LNAs") were successfully applied in primates to silence miR-122. Elmen J., et al., (2008) Nature 452, 896-899, report that efficient silencing of miR-122 was achieved in primates by three doses of 10 mg kg-1 LNA-antimiR, leading to a long-lasting and reversible decrease in total plasma cholesterol without any evidence for LNA-associated toxicities or histopathological changes in the study animals.

In some embodiments, the methods described herein can include co-administration with other drugs or pharmaceuticals, e.g., compositions for providing cholesterol homeostasis. For example, the inhibitory nucleic acids can be co-administered with drugs for treating or reducing risk of a disorder described herein.

Delivery of siRNA In Vivo

The overall efficacy of RNAi-based therapies depends on the efficiency of the delivery system to selectively target infected or diseased tissue versus normal non-malignant tissue, and on the stability of the agent within the cell. However, since 1998 when the first human RNAi-based clinical trials occurred, the number of clinical trials involving RNAi therapies targeting the liver has rapidly increased (Sehgal, A et al (2013) J. Hepatology 59:1354-1359). To avoid rapid degradation of unmodified siRNAs in the blood and serum in vivo, chemical modification or conjugate formation (simple or poly-) may be used by those skilled in the art. Examples of modifications may include lipid carriers, such as liposomal vehicles (Kanasty, R et al (2013) Nature Mater. 12, 967-977); Watanabe et al (2007) J. Hepatol 47:744-50; Aleku et al (2008) Cancer Res 68:9788-98; Moreira et al (2008) J. Nanosci Nanotechnol 8:2187-204; cationic carriers, such as cyclodextrin-based cationic polymers (Heidel et al (2007) Clin Cancer Res 13:2207-15) and biodegradable components (Dimitrova et al (2008). In some embodiments, liposome particles (Morrissey, D V et al (2005) Biotechnol 23:1002-1007), PEGylated nanoparticles (Carmona, S et al (2009) Mol Pharm 6:706-717), or Dynamic Poly Conjugate (DPC) (Rozema et al (2007) PNAS 104:12982-12987) may be used to deliver siRNAs to the liver. In some embodiments, this delivery system may feature reversibly masked polymers that are only revealed under specific conditions, such as the acidic environment of the endosome (Rozema et al (2007) PNAS 104:12982-12987). In some embodiments, the delivery system may dependent on the attachment to a liver-specific receptor on the cell surface of hepatocytes, such asialoglycoprotein (Wu, J et al (2002) Front Biosci 7: d717-d725). In some embodiments, the target siRNA may directly be conjugated to cholesterol (Wooddell, C et al (2013) Mol Therapy 21:973-985). In some embodiments hydrodynamic intravenous injections and electrical pulsing may be used to directly deliver RNAi therapeutics (Morrissey et al (2005) Hepatology 41:1349-56; Golzio et al (2005) Gen Ther 12:246-51). RNAi therapeutics may also be delivered via electroporation of purified exosomes (Alvarez-Erviti et al (2011) Nat Biotechnol 29:341-345). For more information on in vivo delivery of RNAi, please see U.S. Ser. No. 12/479,747; U.S. Pat. Nos. 8,501,930, 8,017,804; 8,357,722; 8,314,227; and 7,371,404.

Pharmaceutical Compositions and Methods of Administration

The methods described herein include the use of pharmaceutical compositions comprising an inhibitor of a FXN Repressing Factor (FXN-RF) as an active ingredient.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration.

Pharmaceutical compositions are typically formulated to be compatible with its intended route of administration. Examples of routes of administration include parenteral, e.g., intravenous, intradermal, subcutaneous, oral (e.g., inhalation), transdermal (topical), transmucosal, and rectal administration.

Methods of formulating suitable pharmaceutical compositions are known in the art, see, e.g., *Remington: The Science and Practice of Pharmacy,* 21st ed., 2005; and the books in the series *Drugs and the Pharmaceutical Sciences: A Series of Textbooks and Monographs* (Dekker, NY). For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, NJ) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin. Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof. Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin: an excipient such as starch or lactose, a disintegrating agent such as alginic acid, Primogel, or corn starch: a lubricant such as magnesium stearate or Sterotes: a glidant such as colloidal silicon dioxide: a sweetening agent such as sucrose or saccharin: or a flavoring agent such as peppermint, methyl salicylate, or orange flavoring.

For administration by inhalation, the compounds can be delivered in the form of an aerosol spray from a pressured container or dispenser that contains a suitable propellant, e.g., a gas such as carbon dioxide, or a nebulizer. Such methods include those described in U.S. Pat. No. 6,468,798.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The pharmaceutical compositions can also be prepared in the form of suppositories (e.g., with conventional suppository bases such as cocoa butter and other glycerides) or retention enemas for rectal delivery.

Therapeutic compounds that are or include nucleic acids can be administered by any method suitable for administration of nucleic acid agents, such as a DNA vaccine. These methods include gene guns, bio injectors, and skin patches as well as needle-free methods such as the micro-particle DNA vaccine technology disclosed in U.S. Pat. No. 6,194,389, and the mammalian transdermal needle-free vaccination with powder-form vaccine as disclosed in U.S. Pat. No. 6,168,587. Additionally, intranasal delivery is possible, as described in, inter alia. Hamajima et al., Clin. Immunol. Immunopathol., 88 (2), 205-10 (1998). Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811.

The pharmaceutical compositions can be included in a container, pack, or dispenser together with instructions for administration.

Dosage

An "effective amount" is an amount sufficient to effect beneficial or desired results. For example, a therapeutic amount is one that achieves the desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a therapeutic compound (i.e., an effective dosage) depends on the therapeutic compounds selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments.

Dosage, toxicity and therapeutic efficacy of the therapeutic compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

EXAMPLES

The invention is further described in the following examples, which do not limit the scope of the invention described in the claims.

Example 1

To identify protein kinases that mediate repression of the mutant FXN gene, we performed a candidate-based RNA interference (RNAi) screen using the human kinase shRNA gene family library from The RNAi Consortium (TRC), comprising 4518 shRNAs targeting 781 protein kinases combined into a single shRNA pool. The shRNA pool was transduced into an iPSC line derived from a patient with FRDA (hereafter called FRDA iPSCs). Specifically, we used the FRDA iPSC line GM23404 (hereafter called FRDA (GM23404) iPSCs, obtained from the Coriell Institute for Medical Research), which was derived from an FRDA patient, GM03816, who has alleles of ~330 and 380 GAA·TTC repeats, and exhibits spinal-cerebral degeneration and cardiomyopathy (Ku et al., Cell Stem Cell, 2010, 7 (5): 631-637). At 18 days post-transduction, cells were harvested and stained with an anti-frataxin antibody and FACS sorted for the 0.2% brightest cells. The top 20 candidates were isolated, and genomic DNA was purified, amplified and sequenced to identify shRNAs. Candidates were validated in directed qRT-PCR experiments to analyze FXN transcription in FA (GM23404) iPSCs. We considered a candidate to be positive if at least two unrelated shRNAs directed against the same target resulted in: (1) a statistically significant increase in FXN transcription compared to that obtained with a control non-silencing (NS) shRNA, and (2) decreased mRNA levels of the target gene. Using this approach, we identified 8 protein kinases that epigenetically repress the mutant FXN gene: AGK, PAN3, PIP4K2C, PRKAR2B, RB1CC1, ROCK1, TEX14 and ULK4 (Table 1).

pitulates the difference in FXN transcription between asymptomatic carriers and FRDA patients, and controls for individual variation in gene expression levels. FIG. 1D shows that knockdown of each protein kinase FXN-RF in FRDA (GAA-intact) iPSCs upregulated mutant FXN transcription comparable to that observed in FRDA (GAA-excised) iPSCs.

TABLE 1

List of the 8 protein kinase FXN-RFs and their functions.

| Gene symbol | Gene name | Function |
| --- | --- | --- |
| AGK | acylglycerol kinase | Mitochondrial membrane protein involved in lipid and glycerolipid metabolism |
| PAN3 | poly(A) specific ribonuclease subunit | Regulatory subunit of the poly(A)-nuclease (PAN) deadenylation complex involved in general and miRNA-mediated mRNA turnover. |
| PIP4K2C | phosphatidylinositol-5-phosphate 4-kinase type 2 gamma | Plays an important role in the production of phosphatidylinositol bisphosphate (PIP2) in the endoplasmic reticulum |
| PRKAR2B | protein kinase cAMP-dependent type II regulatory subunit beta | Regulatory subunit of CAMP-dependent protein kinase. Type II regulatory chains mediate membrane association by binding to anchoring proteins, including MAP2 kinase. |
| RB1CC1 | RB1 inducible coiled-coil 1 | Involved in a variety of cell processes including cell growth, cell proliferation, apoptosis, autophagy and cell migration. Potent regulator of the RB1 pathway. |
| ROCK1 | rho associated coiled-coil containing protein kinase 1 | Serine/threonine kinase and major effector of the small GTPase RhoA. Involved in regulation of smooth muscle contraction, actin cytoskeleton organization, stress fiber and focal adhesion formation, neurite retraction, cell adhesion and motility via phosphorylation of DAPK3, GFAP, LIMK1, LIMK2, MYL9/MLC2, PFN1 and PPP1R12A. |
| TEX14 | testis expressed 14, intercellular bridge forming factor | Required for the formation of intercellular bridges in germ cells, which are required for spermatogenesis. |
| ULK4 | unc-51 like kinase 4 | Serine/threonine kinase likely involved in neurite branching, neurite elongation and neuronal migration. |

FIGS. 1A and B show that knockdown of each of these 8 protein kinases in FRDA (GM23404) iPSCs upregulated mutant FXN transcription, resulting in FXN mRNA levels comparable to that observed in an iPSC line derived from a normal individual (BJ1-iPS4 cells (Sheridan et al., PLOS One, 2011, 6 (10):e26203); hereafter called normal iPSCs). The immunoblot of FIG. 1C shows that knockdown of each protein kinase also increased frataxin levels comparable to that observed in normal iPSCs.

To confirm these results, we obtained an isogenic pair of FRDA iPSC lines in which the GAA·TTC repeat is either intact (GAA-intact) or has been deleted on one allele (GAA-excised) (Li et al., Mol Ther, 2015, 23 (6): 1055-1065). The cell lines were derived from an FRDA patient, FRDA68, who has alleles of ~1400 and 560 GAA·TTC repeats: the GAA-excised derivative contains only the allele with 560 repeats and thus provides a control for FXN transcription levels in an asymptomatic carrier. This pair of isogenic FRDA cell lines is a powerful experimental tool that reca- We next asked whether inhibition of the 8 protein kinase FXN-RFs would also upregulate transcription of the mutant FXN gene in post-mitotic neurons and cardiomyocytes, the cell types most relevant to FRDA. To derive post-mitotic FRDA neurons, FRDA (GM23404) iPSCs were stably transduced with lentiviral vectors expressing Neurogenin-1 and Neurogenin-2 to promote neuronal differentiation, according to published methods (Busskamp et al., Mol Syst Biol, 2014, 10:760); for convenience, we refer to these cells as FRDA neurons. Treatment of FRDA neurons with an shRNA targeting any one of the 8 protein kinase FXN-RFs upregulated mutant FXN transcription and increased frataxin to levels comparable to that of normal neurons (FIGS. 2A,B)

To derive FRDA cardiomyocytes, FRDA (GM23404) iPSCs were cultured for two days with chemically defined medium ("CDM3", consisting of RPMI 1640 medium, albumin and ascorbic acid) supplemented with the GSK3ß inhibitor and Wnt signaling activator CHIR99021, then cultured for two days with CDM3 supplemented with the Wnt inhibitor Wnt-C59, and finally cultured with CDM3 alone, as previously described (Burridge et al., PLOS One, 2011, 6 (4):e18293. Ten days post-differentiation, beating colonies were dissociated and re-seeded to derive single cardiomyocytes: for convenience, we refer to these cells as FRDA cardiomyocytes. Treatment of FRDA cardiomyocytes with an shRNA targeting any one of the 8 protein kinase FXN-RFs upregulated mutant FXN transcription and increased frataxin to levels comparable to that of normal cardiomyocytes (FIGS. 2C, D).

We next asked whether FXN-RF inhibition could ameliorate two characteristic mitochondrial defects of FRDA neurons and cardiomyocytes: increased levels of reactive oxygen species (ROS) and decreased oxygen consumption. In the first set of experiments, FRDA neurons and cardiomyocytes expressing a protein kinase FXN-RF shRNA were stained with MitoSOX (an indicator of mitochondrial superoxide levels and mitochondrial ROS production) followed by flow cytometry analysis. As expected. FRDA neurons and cardiomyocytes had increased levels of mitochondrial ROS production compared to normal neurons and cardiomyocytes (FIGS. 3A, B). Notably, treatment of FRDA neurons and cardiomyocytes with an shRNA targeting any one of the 8 protein kinase FXN-RFs substantially decreased mitochondrial ROS production (FIGS. 3A, B). In the second set of experiments, we measured mitochondrial oxygen consumption rate, which is related to ATP production, using an Agilent Seahorse XF Analyzer [63]. As expected, mitochondrial oxygen consumption rate in FRDA neurons and cardiomyocytes was ~60% of the level observed in normal neurons and cardiomyocytes (FIGS. 3C, D). Notably, treatment of FRDA neurons and cardiomyocytes with an shRNA targeting any one of the 8 protein kinase FXN-RFs increased oxygen consumption rate (FIGS. 3C, D).

Of the 8 new FXN-RFs that we identified, we are particularly enthusiastic about ROCK1, a serine-threonine kinase and major effector of the small GTPase RhoA (Schofield and Bernard, Crit Rev Biochem Mol Biol, 2013, 48 (4): 301-316. ROCK1 phosphorylates a variety of substrates, some of which can affect cell signaling pathways, such as PI3K/AKT (Ruth et al., J Invest Dermatol, 2006, 126 (4): 862-868), and transcription factors, such as NF-kB (Shimizu et al., Mol Hum Reprod, 2007, 13 (3): 181-187) and Runx2 (Huang et al., Exp Ther Med, 2018, 15 (5): 4457-4464). In addition to ROCK1, mammalian cells express another ROCK isoform encoded by a distinct gene, ROCK2. Notably, although both ROCK isoforms are ubiquitously expressed in all adult tissues, ROCK2 is the dominant isoform in the brain and heart (Koch et al., Pharmacol Ther, 2018, 189:1-21). ROCK1 and ROCK2 share ~65% overall amino acid identity and 92% identity in their kinase domains, with 100% identity within their ATP-binding pockets (Nakagawa et al., FEBS Lett, 1996, 392 (2): 189-193; Takahashi et al., Genomics, 1999, 55 (2): 235-237). The strong homology between ROCK1 and ROCK2 suggested that ROCK2 might also be an FXN-RF and raised the possibility that the two ROCK1 shRNAs used in the previous experiments described above (hereafter called ROCK1-1 and ROCK1-2 shRNAs) might also knock down ROCK2. Indeed, we found that the ROCK1-1 and ROCK1-2 shRNAs knocked down both ROCK1 and ROCK2 (FIG. 4A). We therefore analyzed additional shRNAs and identified a ROCK1 shRNA (ROCK1-3) that knocked down ROCK1 but not ROCK2, and a ROCK2 shRNA that knocked down ROCK2 but not ROCK1 (FIG. 4B). FIGS. 4C-E show that selective knockdown of either ROCK1 or ROCK2 upregulated mutant FXN transcription in FRDA iPSCs, post-mitotic neurons and cardiomyocytes. Thus, both ROCK1 and ROCK2 are protein kinase FXN-RFs.

Because of the high identity in the kinase domains, the vast majority of ROCK inhibitors inhibit both ROCK1 and ROCK2 (Feng et al., J Med Chem, 2016, 59 (6): 2269-2300). ROCK1/2 inhibitors are being actively investigated as therapeutics in a wide variety of pathological conditions including asthma, cancer, erectile dysfunction, glaucoma, cardiac and vascular conditions, insulin resistance, and fibrosis (Feng et al., J Med Chem, 2016, 59 (6): 2269-2300). A number of ROCK1/2 inhibitors have been found to be safe in phase 1 clinical trials and some have progressed to phase 2 and 3 clinical trials in the US (Feng et al., J Med Chem, 2016, 59 (6): 2269-2300). To date, two ROCK1/2 inhibitors, fasudil and ripasudil, have been approved for clinical use in Japan and fasudil has also been approved in China. Fasudil is approved for the treatment of cerebral vasospasm (Knipe et al., Pharmacol Rev, 2015, 67 (1): 103-117), and has also been extensively evaluated for treatment of stable angina (Vicari et al., J Am Coll Cardiol, 2005, 46 (10): 1803-1811), and ripasudil is approved for the treatment of glaucoma (Garnock-Jones, Drugs, 2014, 74 (18): 2211-2215). Both fasudil and ripasudil are orally active and well tolerated without adverse effects (Vicari et al., J Am Coll Cardiol, 2005, 46 (10): 1803-1811; Garnock-Jones, Drugs, 2014, 74 (18): 2211-2215; Knipe et al., Pharmacol Rev, 2015, 67 (1): 103-117).

FIGS. 5A-F shows that treatment with fasudil, ripasudil or another ROCK1/2 inhibitor, Y27632 (Uehata et al., Nature, 1997, 389 (6654): 990-994), upregulated transcription of the mutant FXN gene and restored FXN mRNA and frataxin protein to normal levels in FRDA iPSCs, neurons and cardiomyocytes. As expected, the upregulation of the mutant FXN gene by ROCK1/2 inhibitors was dose-dependent (FIG. 5G). Upregulation of the mutant FXN gene in FRDA neurons following treatment with either the ROCK1/2 inhibitor fasudil or the selective ROCK2 inhibitor KD025 (Boerma et al., Blood Coagul Fibrinolysis, 2008, 19 (7): 709-718) was confirmed using the highly quantitative method of massively parallel short-read sequencing (also called RNA-sequencing or RNA-seq) on the Illumina platform (FIG. 5H).

Finally, we asked whether ROCK1/2 inhibitors could ameliorate characteristic mitochondrial defects of FRDA neurons and cardiomyocytes. Treatment of FRDA neurons and cardiomyocytes with fasudil, ripasudil or Y27632 resulted in decreased mitochondrial ROS production (FIGS. 6A, B) and increased mitochondrial oxygen consumption rate (FIGS. 6C, D). Mitochondrial dysfunction results in reduced levels of several mitochondrial Fe—S proteins, such as aconitase 2 (ACO2) and iron-sulfur cluster assembly enzyme (ISCU) (Urrutia et al., Front Pharmacol, 5:38). FIGS. 6E-F show that treatment of FRDA neurons and cardiomyocytes with fasudil, ripasudil or KD025 resulted in increased levels of ACO2 and ISCU comparable to that observed in normal neurons and cardiomyocytes.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating a subject having a disorder associated with a mutation in the FXN gene and having reduced expression of frataxin protein, the method comprising administering to the subject a therapeutically effective amount of an inhibitor of rho associated coiled-coil containing protein kinase 1 (ROCK1) or rho associated coiled-coil containing protein kinase 2 (ROCK2).

2. The method of claim 1, wherein the subject has Friedreich ataxia (FRDA).

3. The method of claim 1, wherein the inhibitor is an inhibitor of ROCK1/2.

4. The method of claim 3, wherein the inhibitor of ROCK1/2 is a small molecule inhibitor of ROCK1/2.

5. The method of claim 4, wherein the small molecule inhibitor of ROCK1/2 is Y27632.

6. The method of claim 4, wherein the small molecule inhibitor of ROCK1/2 is fasudil or ripasudil.

7. The method of claim 4, wherein the small molecule inhibitor of ROCK1/2 is a cyclohexanecarboxamide; a dihydropyrimidinone or dihydropyrimidine; a ureidobenzamide; Thiazovivin; GSK429286A; RKI-1447; GSK180736A; Hydroxyfasudil; OXA 06; Y-39983; Netarsudil; GSK269962; an indazole; an isoquinoline sulfonyl; 5-(1,4-diazepan-1-ylsulfonyl)isoquinoline; KD025; XD-4000; SR 3677; AS 1892802; H-1152; N-(4-Pyridyl)-N'-(2,4,6-trichlorophenyl)urea); 3-(4-Pyridyl)-1H-indole; a 3-[2-(aminomethyl)-5-[(pyridin-4-yl)carbamoyl]phenyl]benzoate; AMA0076; TC-S 7001; AT13148; an inhibitor with the scaffold 4-Phenyl-1H-pyrrolo[2,3-b]pyridine; a heterocyclic amino; pyridylthiazole urea; or a quinazoline; and pharmaceutically acceptable salts thereof.

8. The method of claim 7, wherein the cyclohexanecarboxamide is Y-27632 or Y-30131.

9. The method of claim 7, wherein the dihydropyrimidinone or dihydropyrimidine is a bicyclic dihydropyrimidinecarboxamide.

10. The method of claim 7, wherein the ureidobenzamide is CAY10622.

11. The method of claim 7, wherein the inhibitor with the scaffold 4-Phenyl-1H-pyrrolo[2,3-b]pyridine is compound TS-f22.

12. The method of claim 1, wherein the inhibitor is an inhibitory nucleic acid that targets and specifically reduces expression of ROCK1 and/or ROCK2.

13. The method of claim 12, wherein the inhibitory nucleic acid is a small interfering RNA, small hairpin RNA, or antisense oligonucleotide.

14. The method of claim 12, wherein the inhibitory nucleic acid is modified.

15. A method of treating a subject having a disorder associated with a mutation in the FXN gene and having reduced expression of frataxin protein, the method comprising administering to the subject a therapeutically effective amount of an inhibitor of expression of a FXN Repressing Factor (FXN-RF) selected from the group consisting of acylglycerol kinase (AGK); poly(A) specific ribonuclease subunit (PAN3); phosphatidylinositol-5-phosphate 4-kinase type 2 gamma (PIP4K2C); protein kinase cAMP-dependent type II regulatory subunit beta (PRKAR2B); RB1 inducible coiled-coil 1 (RB1CC1); testis expressed 14, intercellular bridge forming factor (TEX14); and unc-51 like kinase 4 (ULK4).

16. The method of claim 15, wherein the subject has Friedreich ataxia (FRDA).

* * * * *

SEQUENCE LISTING

<160> NUMBER OF SEQ ID NOS: 21

<210> SEQ ID NO 1
<211> LENGTH: 59
<212> TYPE: DNA
<213> ORGANISM: Artificial Sequence
<220> FEATURE:
<223> OTHER INFORMATION: hairpin sequence

<400> SEQUENCE: 1
ccggccattg aactgtccat cacaactcga gttgtgatgg acagttcaat ggttttttg      59

<210> SEQ ID NO 2
<211> LENGTH: 59
<212> TYPE: DNA
<213> ORGANISM: Artificial Sequence
<220> FEATURE:
<223> OTHER INFORMATION: hairpin sequence

<400> SEQUENCE: 2
ccggcctcaa ctgtacttgg agaaactcga gtttctccaa gtacagttga ggttttttg      59

<210> SEQ ID NO 3
<211> LENGTH: 59
<212> TYPE: DNA
<213> ORGANISM: Artificial Sequence
<220> FEATURE:
<223> OTHER INFORMATION: hairpin sequence

<400> SEQUENCE: 3
ccggcctcaa ctgtacttgg agaaactcga gtttctccaa gtacagttga ggttttttg      59

<210> SEQ ID NO 4
<211> LENGTH: 58
<212> TYPE: DNA
<213> ORGANISM: Artificial Sequence
<220> FEATURE:
<223> OTHER INFORMATION: hairpin sequence

<400> SEQUENCE: 4
ccggcgttat ctgttgaaac tctttctcga gaaagagttt caacagataa cgttttg        58

<210> SEQ ID NO 5
<211> LENGTH: 58
<212> TYPE: DNA
<213> ORGANISM: Artificial Sequence
<220> FEATURE:
<223> OTHER INFORMATION: hairpin sequence

<400> SEQUENCE: 5
ccggcgcttc cttatctcct acgatctcga gatcgtagga gataaggaag cgttttg        58

<210> SEQ ID NO 6
<211> LENGTH: 58
<212> TYPE: DNA
<213> ORGANISM: Artificial Sequence
<220> FEATURE:
<223> OTHER INFORMATION: hairpin sequence

<400> SEQUENCE: 6
ccggccttac acagtatgat gccaactcga gttggcatca tactgtgtaa ggttttg        58

<210> SEQ ID NO 7
<211> LENGTH: 58
<212> TYPE: DNA
<213> ORGANISM: Artificial Sequence

```
<220> FEATURE:
<223> OTHER INFORMATION: hairpin sequence

<400> SEQUENCE: 7
ccggcctgaa agtagtagat gtgatctcga gatcacatct actactttca ggtttttg          58

<210> SEQ ID NO 8
<211> LENGTH: 58
<212> TYPE: DNA
<213> ORGANISM: Artificial Sequence
<220> FEATURE:
<223> OTHER INFORMATION: hairpin sequence

<400> SEQUENCE: 8
ccgggtccag gattatacat ccaaactcga gtttggatgt ataatcctgg acttttg           58

<210> SEQ ID NO 9
<211> LENGTH: 57
<212> TYPE: DNA
<213> ORGANISM: Artificial Sequence
<220> FEATURE:
<223> OTHER INFORMATION: hairpin sequence

<400> SEQUENCE: 9
ccgggctgtg aatgagtttg taatactcga gtattacaaa ctcattcaca gcttttt           57

<210> SEQ ID NO 10
<211> LENGTH: 57
<212> TYPE: DNA
<213> ORGANISM: Artificial Sequence
<220> FEATURE:
<223> OTHER INFORMATION: hairpin sequence

<400> SEQUENCE: 10
ccgggcaaag aaattaggga atcttctcga gaagattccc taatttcttt gcttttt           57

<210> SEQ ID NO 11
<211> LENGTH: 58
<212> TYPE: DNA
<213> ORGANISM: Artificial Sequence
<220> FEATURE:
<223> OTHER INFORMATION: hairpin sequence

<400> SEQUENCE: 11
ccggcgggtt gttcagattg agaaactcga gtttctcaat ctgaacaacc cgtttttg         58

<210> SEQ ID NO 12
<211> LENGTH: 58
<212> TYPE: DNA
<213> ORGANISM: Artificial Sequence
<220> FEATURE:
<223> OTHER INFORMATION: hairpin sequence

<400> SEQUENCE: 12
ccgggcattc caagatgatc gttatctcga gataacgatc atcttggaat gctttttg         58

<210> SEQ ID NO 13
<211> LENGTH: 58
<212> TYPE: DNA
<213> ORGANISM: Artificial Sequence
<220> FEATURE:
<223> OTHER INFORMATION: hairpin sequence

<400> SEQUENCE: 13
ccgggcacca gttgtacccg atttactcga gtaaatcggg tacaactggt gctttttg         58
```

```
<210> SEQ ID NO 14
<211> LENGTH: 58
<212> TYPE: DNA
<213> ORGANISM: Artificial Sequence
<220> FEATURE:
<223> OTHER INFORMATION: hairpin sequence

<400> SEQUENCE: 14
ccgggcacca gttgtacccg atttactcga gtaaatcggg tacaactggt gctttttg       58

<210> SEQ ID NO 15
<211> LENGTH: 58
<212> TYPE: DNA
<213> ORGANISM: Artificial Sequence
<220> FEATURE:
<223> OTHER INFORMATION: hairpin sequence

<400> SEQUENCE: 15
ccggcctacc aagatttcca agaatctcga gattcttgga atcttggta ggtttttg        58

<210> SEQ ID NO 16
<211> LENGTH: 58
<212> TYPE: DNA
<213> ORGANISM: Artificial Sequence
<220> FEATURE:
<223> OTHER INFORMATION: hairpin sequence

<400> SEQUENCE: 16
ccggccgaaa ccttactatg atattctcga gaatatcata gtaaggtttc ggtttttg       58

<210> SEQ ID NO 17
<211> LENGTH: 57
<212> TYPE: DNA
<213> ORGANISM: Artificial Sequence
<220> FEATURE:
<223> OTHER INFORMATION: hairpin sequence

<400> SEQUENCE: 17
ccggcagggc tttattacag gagaactcga gttctcctgt aataaagccc tgttttt        57

<210> SEQ ID NO 18
<211> LENGTH: 57
<212> TYPE: DNA
<213> ORGANISM: Artificial Sequence
<220> FEATURE:
<223> OTHER INFORMATION: hairpin sequence

<400> SEQUENCE: 18
ccggcgacgg aagggaacaa tcaatctcga gattgattgt tcccttccgt cgttttt        57

<210> SEQ ID NO 19
<211> LENGTH: 4
<212> TYPE: PRT
<213> ORGANISM: Artificial Sequence
<220> FEATURE:
<223> OTHER INFORMATION: peptide inhibitor of ROCK1/2

<400> SEQUENCE: 19

Tyr Ser Pro Ser
1

<210> SEQ ID NO 20
<211> LENGTH: 7
<212> TYPE: PRT
<213> ORGANISM: Artificial Sequence
<220> FEATURE:
```

```
<223> OTHER INFORMATION: peptide inhibitor of ROCK1/2

<400> SEQUENCE: 20

Glu Arg Thr Tyr Ser Pro Ser
1               5

<210> SEQ ID NO 21
<211> LENGTH: 12
<212> TYPE: PRT
<213> ORGANISM: Artificial Sequence
<220> FEATURE:
<223> OTHER INFORMATION: peptide inhibitor of ROCK1/2

<400> SEQUENCE: 21

Glu Arg Thr Tyr Ser Pro Ser Thr Ala Val Arg Ser
1               5                   10
```